(12) United States Patent
Johs et al.

(10) Patent No.: US 7,746,471 B1
(45) Date of Patent: *Jun. 29, 2010

(54) FLYING MOBILE ON-BOARD ELLIPSOMETER, POLARIMETER, REFLECTOMETER AND THE LIKE SYSTEMS

(75) Inventors: Blaine D. Johs, Lincoln, NE (US); Ping He, Lincoln, NE (US); Martin M. Liphardt, Lincoln, NE (US); Christopher A. Goeden, Lincoln, NE (US); John A. Woollam, Lincoln, NE (US); James D. Welch, Omaha, NE (US)

(73) Assignee: J.A Woollam Co., Inc., Lincoln, NE (US)

( * ) Notice: Subject to any disclaimer, the term of this patent is extended or adjusted under 35 U.S.C. 154(b) by 477 days.

This patent is subject to a terminal disclaimer.

(21) Appl. No.: 11/890,391

(22) Filed: Aug. 5, 2007

Related U.S. Application Data

(60) Continuation-in-part of application No. 11/105,852, filed on Apr. 14, 2005, now Pat. No. 7,277,171, application No. 11/890,391, and a continuation-in-part of application No. 10/925,333, filed on Aug. 24, 2004, now Pat. No. 7,265,838, and a continuation-in-part of application No. 10/829,620, filed on Apr. 22, 2004, now Pat. No. 7,193,710, and a division of application No. 10/050,802, filed on Jan. 15, 2002, now Pat. No. 6,859,278, application No. 11/890,391, and a continuation-in-part of application No. 10/857,774, filed on May 28, 2004, now Pat. No. 7,274,450, and a continuation-in-part of application No. 10/699,540, filed on Nov. 1, 2003, now Pat. No. 7,158,231, application No. 11/890,391, and a continuation-in-part of application No. 11/704,545, filed on Feb. 10, 2007, now Pat. No. 7,426,030, and a continuation-in-part of application No. 11/145,470, filed on Jun. 6, 2005, now Pat. No. 7,327,456, and a continuation-in-part of application No. 10/376,677, filed on Feb. 28, 2003, now Pat. No. 6,982,792, and a continuation-in-part of application No. 10/178,723, filed on Jun. 24, 2002, now Pat. No. 6,950,182, and a continuation-in-part of application No. 09/864,840, filed on May 24, 2001, now Pat. No. 6,456,376, and a continuation-in-part of application No. 09/854,548, filed on May 14, 2001, now abandoned, and a continuation-in-part of application No. 09/583,229, filed on May 30, 2000, now Pat. No. 6,804,004, and a continuation-in-part of application No. 09/531,877, filed on Mar. 21, 2000, now Pat. No. 6,535,286, application No. 11/890,391, and a continuation-in-part of application No. 10/849,740, filed on May 20, 2004, now Pat. No. 7,385,697.

(60) Provisional application No. 60/836,232, filed on Aug. 9, 2006, provisional application No. 60/564,747, filed on Apr. 23, 2004, provisional application No. 60/580,314, filed on Jun. 17, 2004, provisional application No. 60/424,589, filed on Nov. 7, 2002, provisional application No. 60/427,043, filed on Nov. 18, 2002, provisional application No. 60/480,851, filed on Jun. 24, 2003, provisional application No. 60/772,926, filed on Feb. 13, 2006, provisional application No. 60/424,589, filed on Nov. 7, 2002, provisional application No. 60/427,043, filed on Nov. 18, 2002, provisional application No. 60/431,489, filed on Dec. 6, 2002, provisional application No. 60/261,243, filed on Jan. 16, 2001, provisional application No. 60/263,874, filed on Jan. 25, 2001, provisional application No. 60/287,784, filed on May 2, 2001, provisional application No. 60/300,714, filed on Jun. 26, 2001, provisional application No. 60/564,747, filed on Apr. 23, 2004, provisional application No. 60/580,314, filed on Jun. 17, 2004.

(51) Int. Cl.
*G01J 4/00* (2006.01)
(52) U.S. Cl. ..................................... 356/369
(58) Field of Classification Search ................. None
See application file for complete search history.

(56) References Cited

U.S. PATENT DOCUMENTS

| | | | | |
|---|---|---|---|---|
| 3,874,797 | A | 4/1975 | Hasai | 356/369 |
| 4,053,232 | A | 10/1977 | Dill | 356/118 |
| 4,647,207 | A | 3/1987 | Bjorh et al. | 356/369 |
| 4,668,086 | A | 5/1987 | Rosencwais et al. | 356/33 |
| 4,672,196 | A | 6/1987 | Canino | 250/225 |
| 5,229,833 | A | 7/1993 | Stewart | 356/364 |
| 5,329,357 | A | 7/1994 | Bernoux et al. | 356/369 |
| 5,343,293 | A | 8/1994 | Berger et al. | 356/369 |
| 5,410,409 | A | 4/1995 | Ray | 356/369 |
| 5,412,473 | A | 5/1995 | Rosencwais et al. | 356/451 |
| 5,438,415 | A * | 8/1995 | Kazama et al. | 356/369 |
| 5,504,582 | A | 4/1996 | Johs et al. | 356/369 |
| 5,521,706 | A | 5/1996 | Green et al. | 356/369 |
| 5,581,350 | A | 12/1996 | Chen et al. | 356/369 |
| 5,582,646 | A | 12/1996 | Woollam et al. | 118/708 |
| 5,596,406 | A | 1/1997 | Rosencwais et al. | 356/327 |
| 5,666,201 | A | 9/1997 | Johs et al. | 356/369 |
| 5,706,087 | A | 1/1998 | Thompson | 356/364 |
| 5,706,212 | A | 1/1998 | Thompson et al. | 356/367 |
| 5,757,494 | A | 5/1998 | Green et al. | 356/369 |
| 5,764,365 | A | 6/1998 | Finarov | 356/630 |
| 5,872,630 | A | 2/1999 | Johs et al. | 356/359 |
| 5,963,327 | A | 10/1999 | He | 356/369 |
| 6,008,906 | A | 12/1999 | Mavis | 356/432 |
| 6,031,614 | A | 2/2000 | Michaelis et al. | 356/369 |
| 6,034,777 | A | 3/2000 | Johs et al. | 356/369 |
| 6,081,334 | A | 6/2000 | Grimbersen et al. | 356/499 |
| 6,721,052 | B2 | 4/2004 | Zhao et al. | 356/369 |
| 6,813,026 | B2 | 11/2004 | McAninch | |
| 7,277,171 | B1 * | 10/2007 | Johs et al. | 356/369 |

* cited by examiner

*Primary Examiner*—Tu T Nguyen
(74) *Attorney, Agent, or Firm*—James D. Welch

(57) ABSTRACT

A substantially self-contained "on-board" material system investigation system for effecting relative translational and rotational motion between a source and detector of electromagnetic radiation and a sample, which system is functionally mounted on a three dimensional locational system to enable positioning at desired locations on, and distances from, the surface of a sample, including the capability to easily and conveniently effect rotation and/or to change the angle-of-incidence of a beam of electromagnetic radiation onto a sample surface and/or to provide gas flow confined in a mini-chamber near the surface of a sample, at a location at which a beam having UV, VUV, IR and/or NIR wavelengths of electromagnetic radiation is caused to be impinged thereupon.

32 Claims, 22 Drawing Sheets

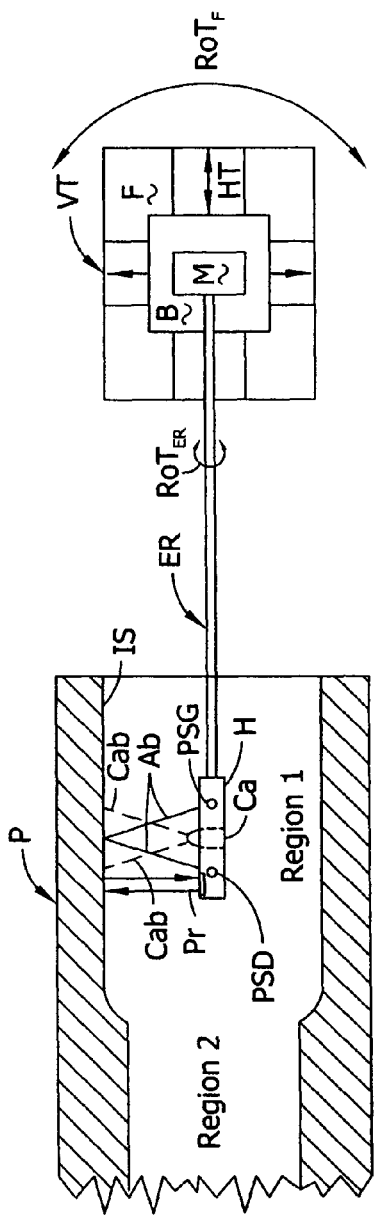
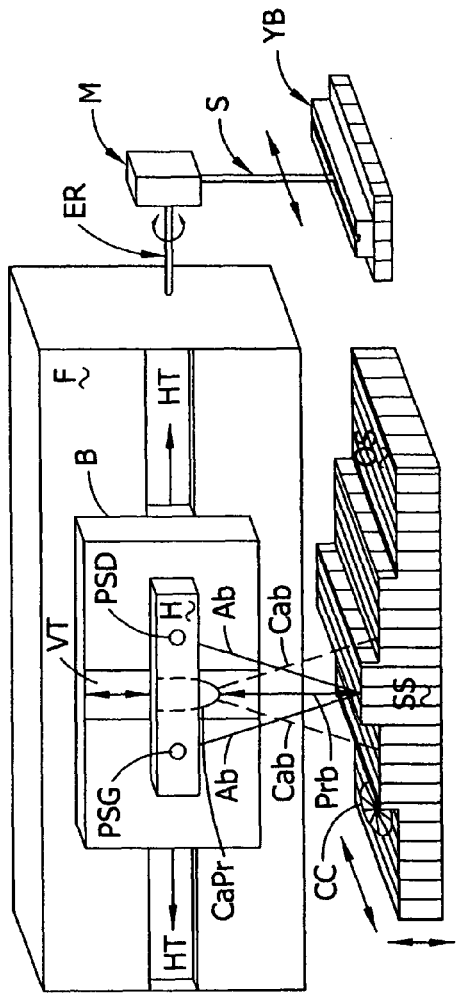
FIG. 1d
FIG. 1c

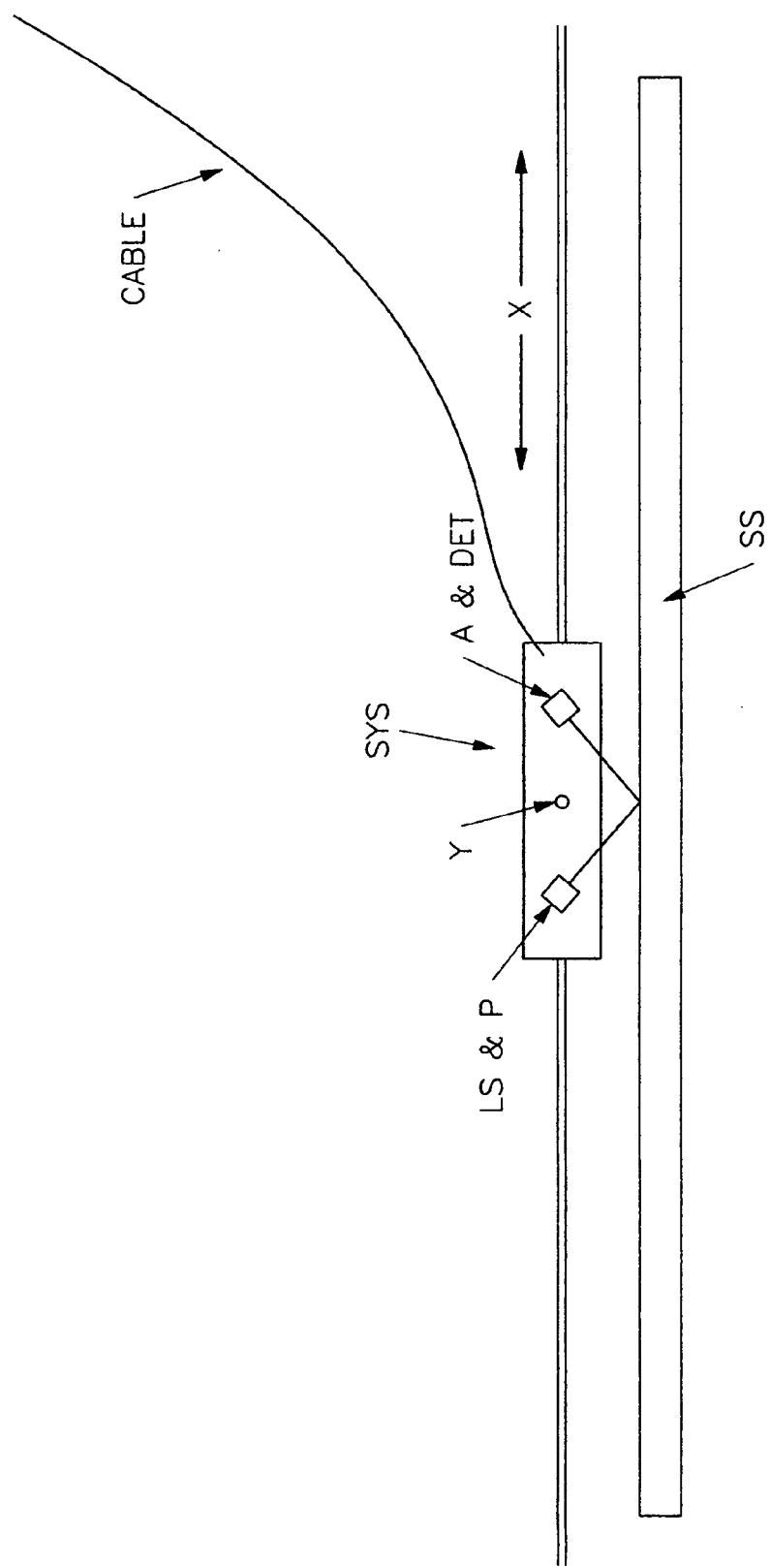

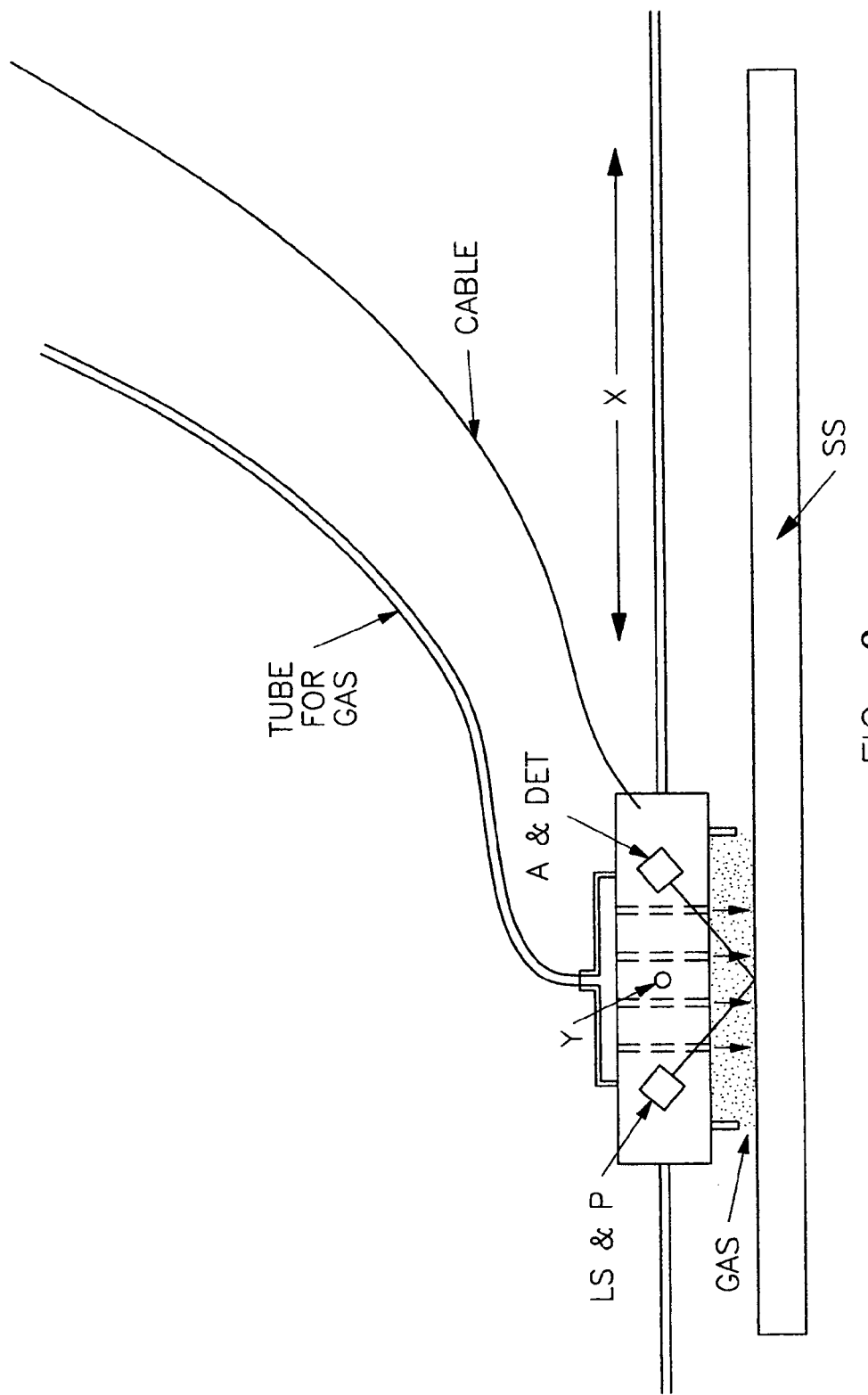

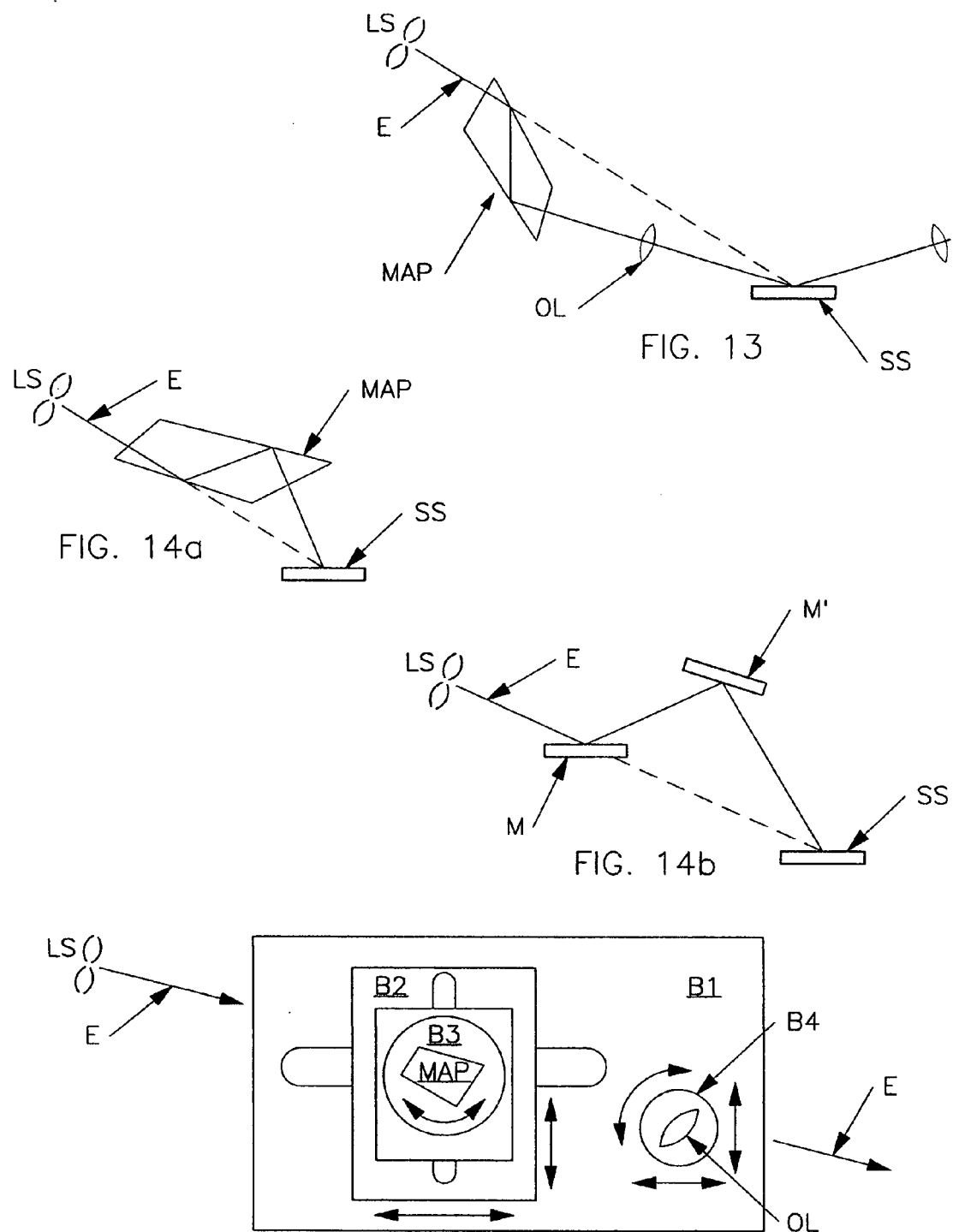

FLYING MOBILE ON-BOARD ELLIPSOMETER, POLARIMETER, REFLECTOMETER AND THE LIKE SYSTEMS

This Application directly Claims Benefit of Provisional Application Ser. No. 60/836,232 filed Aug. 9, 2006. This Application is directly a CIP of patent application Ser. No. 11/105,852 filed Apr. 14, 2005 now U.S. Pat. No. 7,277,171, and therevia this Application Claims benefit of Provisional Applications 60/564,747 Filed Apr. 23, 2004, and 60/580,314 Filed Jun. 17, 2004. This Application is further a Continuation-In-Part of Utility application Ser. Nos. 10/829,620 Filed Apr. 22, 2004 now U.S. Pat. No. 7,193,710; and of 10/925, 333 Filed Aug. 24, 2004 now U.S. Pat. No. 7,265,838, and therevia of 10/050,802 Filed Jan. 15, 2002, (now U.S. Pat. No. 6,859,278). This Application is further a Continuation-In-Part of Utility application Ser. No. 10/925,333 Filed Aug. 24, 2004 now U.S. Pat. No. 7,265,838, and of 10/829,620 Filed Apr. 22, 2004, and is a Divisional of 10/050,802 Filed Jan. 15, 2002 now U.S. Pat. No. 6,859,278; and via the above Applications Claims Benefit of Provisional Applications Ser. No. 60/261,243 Filed Jan. 16, 2001, 60/263,874 Filed Jan. 25, 2001, 60/287,784 Filed May 2, 2001. This Application is further a CIP of Utility application Ser. Nos. 10/699,540 Filed Nov. 1, 2003 now U.S. Pat. No. 7,158,231, and 10/857,774 Filed May 28, 2004 now U.S. Pat. No. 7,247,450, and therevia Claims benefit of Provisional Applications 60/424,589 Filed Nov. 7, 2002, 60/427,043 Filed Nov. 18, 2002, and 60/480, 851 Filed Jun. 24, 2003. This Application is further directly a CIP of application Ser. No. 11/704,545 Filed Feb. 10, 2007 now U.S. Pat. No. 7,426,030 and therevia Claims Benefit of Provisional Application Ser. No. 60/772,926 Filed Feb. 13, 2006; and is a CIP of application Ser. No. 11/145,470. Filed Jun. 6, 2005 now U.S. Pat. No. 7,327,456, and therevia of Ser. No. 10/376,677 Filed Feb. 28, 2003 now U.S. Pat. No. 6,982, 792 and from Ser. No. 09/531,877 Filed Mar. 21, 2000 now U.S. Pat. No. 6,535,286; and from Ser. No. 10/178,723 filed Jun. 24, 2002 now U.S. Pat. No. 6,950,182; and Ser. No. 09/583,229 filed May 30, 2000 now U.S. Pat. No. 6,804,004; and from Ser. No. 09/864,840 filed May 24, 2001 now U.S. Pat. No. 6,456,376; and Ser. No. 09/845,548 filed May 14, 2001 now abandoned; and Claims benefit of Provisional Application Ser. Nos. 60/300,714 filed Jun. 26, 2001, and 60/424,589 filed Nov. 7, 2002, and 60/427,043 filed Nov. 18, 2002 and 60/431,489 filed Dec. 6, 2002. This Application also is a CIP of application Ser. No. 10/849,740 Filed May 20, 2004 now U.S. Pat. No. 7,385,697. This Application is also a CIP of Pending application Ser. No. 11/105,852 Filed Apr. 14, 2005 also therevia Claims benefit of Provisional Applications 60/564,747 Filed Apr. 23, 2004, and 60/580,314 Filed Jun. 17, 2004. This Application is further a Continuation-In-Part of Utility application Ser. Nos. 10/829,620 Filed Apr. 22, 2004; and of 10/925,333 Filed Aug. 24, 2004, and therevia of 10/050,802 Filed Jan. 15, 2002, (now U.S. Pat. No. 6,859, 278). This Application is further a Continuation-In-Part of Utility application Ser. No. 10/925,333 Filed Aug. 24, 2004, and of 10/829,620 Filed Apr. 22, 2004, and is a Divisional of 10/050,802 Filed Jan. 15, 2002; and via the above Applications Claims Benefit of Provisional Application Ser. No. 60/261,243 Filed Jan. 16, 2001, 60/263,874 Filed Jan. 25, 2001, 60/287,784 Filed May 2, 2001.

TECHNICAL FIELD

Pending patent application Ser. No. 11/105,852, Filed Apr. 14, 2005 with Priority back to Apr. 23, 2004 via Provisional Application Ser. No. 60/564,747, describes a substantially self contained flying ellipsometer, polarimeter, reflectometer or spectrophotometer system that provides for moving a combined source and detector of electromagnetic radiation over the a surface of a sample in two, (eg. "X" and "Y"), orthogonal dimensions to enable positioning it at desired locations on, and offset distance from sample in a "Z" dimension corresponding to a distance between said combined source and detector and said sample, and which enables easy sequential setting of different Angles-of-Incidence of a beam of electromagnetic radiation to a surface of said sample. Added by the present invention is the capability of rotating said combined source and detector about at least one axis and to provide gas confined in a "mini-chamber" near the surface of a sample, at a location at which a beam of electromagnetic radiation is caused to be impinged thereupon.

BACKGROUND

For general insight it is noted that Ellipsometer Systems generally include a source of a beam of electromagnetic radiation, a Polarizer, which serves to impose a known, (typically linear), state of polarization on a beam of electromagnetic radiation, a Stage for supporting a sample, and an Analyzer which serves to select a polarization state in a beam of electromagnetic radiation after it has interacted with a material system, and pass it to a Detector System for analysis therein. As well, one or more Compensator(s) can be present and serve to affect a phase retardance between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed, and that provides benefit in that polarization state sensitivity to input and output optics during data acquisition is essentially nonexistent. This enables relatively easy use of optic fibers, mirrors, lenses etc. for input/output.

Typical construction of spectrophotometer, reflectometer, polarimeter, ellipsometer and the like systems, (eg. Rotating Analyzer, Rotating Polarizer, Rotating Compensator, Modulator Element Ellipsometer) provides a Sample Supporting Stage which is substantially fixed in location. Functionally oriented with respect thereto are a Substantially Fixed Position Source Means (S) for providing a beam of electromagnetic radiation at an oblique angle to said Sample Supporting Stage, and a Substantially Fixed Position Data Detector Means (D) for intercepting Electromagnetic Radiation which Reflects (or Transmits through), a Sample placed on said Sample Supporting Stage. Typical procedure is to place a Sample onto the Sample Supporting Stage, cause a beam of Electromagnetic Radiation to impinge thereonto, and record data produced by the Data Detector Means in response to electromagnetic radiation which enters thereinto, which data is analyzed to provide insight into Sample Optical and Physical properties. Said procedure can include adjustment of the Sample Supporting Stage, or the source and detector of electromagnetic radiation in an "X"-"Y" Plane, and along a "Z" direction perpendicular to its surface, (ie. a vertical position adjustment where the Electromagnetic Radiation approaches the Sample at an oblique angle from a laterally located Source). This purpose of said "Z" adjustment is, for instance, to enable the directing of a beam of Electromagnetic Radiation Reflected from a Sample placed on said Sample Supporting Stage into the Data Detector without moving the Data Detector so it intercepts a beam exiting said Sample. It should be appreciated then that conventional Reflectometer, Ellipsometer and Polarimeter Systems which include provision for such Sample positioning adjustment and orientation with respect to an impinging Electromagnetic beam, typically do so by allowing the Sample Supporting Stage position to be adjusted, rather than by effecting simultaneous change in location of the Source and Data Detector with respect to the Sample Supporting Stage, because it is far simpler to implement Sample Supporting Stage location change. However, an alternative is mount a Reflectometer, Spectrophotometer, Ellipsometer, Polarimeter or the like System to a means for moving it in an "X"-"Y" Plane, and along a "Z" direction perpendicular to its surface of the Sample with respect to a substantially fixed position Stage for supporting a Sample. In either case, however, a relative motion occurs between the Reflectometer, Ellipsometer, Polarimeter or the like System and a sample.

The present invention breaks with conventional practice by, while typically providing a substantially fixed position Stage for supporting a Sample, providing a Reflectometer, Spectrophotometer, Ellipsometer, Polarimeter or the like System which is mounted to a positioning system which allows adjustment its location in an "X"-"Y" Plane, and along a "Z" direction perpendicular to its surface of the Sample. The present invention then, allows investigation of a large Sample at many locations thereof, including rotational capability to allow investigation of Samples of other than flat shapes, including both inner and outer surfaces of, for instance, pipe and/or spherical shaped objects.

Continuing, while present invention systems can be applied in any material system investigation system such as Polarimeter, Reflectometer, Spectrophotometer and the like Systems, an important application is in Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system:

$$TAN(\psi)e^{(i\Delta)} = r_p/r_s$$

While Data taken at one (AOI) and one or multiple wavelengths is often sufficient to allow ellipsometric characterization of a sample system, the results of Ellipsometric Investigation can be greatly enhanced by using multiple (AOI's) to obtain additional data sets. However, while it is relatively easy to provide Wavelength change without extensive difficult physical Ellipsometer System Orientation change, it is typically difficult to change the Angle-of-Incidence (AOI) that a Beam of Electromagnetic Radiation makes to a surface of a sample system. An (AOI) change requires that both the Source of the Electromagnetic Beam and the Detector must be re-positioned and aligned, and such is tedious and time consuming. The present invention therefore can provide means to easily effect (AOI) change.

It is also noted that Ultraviolet (UV) or Infra-Red (IR) Wavelengths are absorbed by oxygen or water vapor, hence where they are applied, it is necessary to evacuate or purge at least the region around a sample. In that light it is noted that the present invention can also include means for allowing practice over a wide range of wavelengths.

To provide insight, it is noted that Spectroscopic Ellipsometry (SE) was developed in the early 1970's after single wavelength ellipsometry had gained widespread acceptance. The first (SE) systems provided limited Ultraviolet (UV) to near Infrared (IR) spectral range capability, and with the exception of a few research instruments, this remained the case until the 1990's. Many challenges faced development of (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen is utilized in place of vacuum at wavelengths, typically with an energy less than about 10 ev. The reason (VUV) ellipsometry must be carried out in vacuum or purging gas is that (VUV) wavelengths, are absorbed by oxygen and water vapor. For additional insight it is noted that while present invention systems can be applied in any material system investigation system such as Polarimeter, Reflectometer and the like Systems, an important application is in Ellipsometer Systems, whether monochromatic or spectroscopic, which operate in a ultraviolet (UV), vacuum ultraviolet (VUV), infrared (IR) or near infrared (NIR) wavelength range. It should therefore be understood that Ellipsometry involves acquisition of sample characterizing data at single or multiple Wavelengths, and at one or more Angle(s)-of-Incidence (AOI) of a Beam of Electromagnetic Radiation to a surface of the sample.

As additional background, it is noted that in the mid-1980's a Spectroscopic ellipsometer was constructed at the BESSY Synchrotron in Berlin for application in the (VUV) wavelength range, (eg. 5-35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J.A. Woollam Co. Inc. At present there are approximately twenty-five (VUV) Systems in use worldwide. It is noted that commercial (VUV) instruments, which provided wavelengths down to 146 nm, were introduced in response to the need for bulk material properties at 156 nm, which is utilized in lithography as applied to semiconductor gate oxide production.

It is disclosed that a known Patent which provides for use of VUV wavelength electromagnetic radiation through 10 eV is U.S. Pat. No. 6,414,302 B1 to Freeouf.

Continuing, the practice of ellipsometry, polarimetry, spectrophotometry, reflectometry, scatterometry and the like, using Infrared (IR), (eg. 2-33 micron), and Ultraviolet (UV), (eg. 135-1700 nm), Electromagnetic Radiation Wavelengths, then is, as disclosed above, known. As mentioned, electromagnetic Radiation with wavelengths below about 190 nm is absorbed by atmospheric components such as Oxygen and Water Vapor. Thus, practice of Ellipsometry etc. using (UV) Wavelengths is typically carried out in vacuum or an atmosphere which does not contain oxygen and/or water vapor or other absorbing components. The J.A. Woollam CO. VUV-VASE, (Registered Trademark), for instance, utilizes a substantially enclosed Chamber which encompasses a substantially enclosed space which during use is purged by Nitrogen and/or Argon or functionally equivalent gas. (Note Nitrogen does not significantly absorb UV Range wavelengths, and Argon is in some respects even a better choice). A problem with practicing Ellipsometry etc. however, where the sample is in a substantially enclosed, internal ambient controlled, chamber is that it is often inconvenient to access what is contained therewithin without entering oxygen or water vapor etc. thereinto. As a result, the J.A. Woollam Co. VUV-VASE, (Registered Trademark), System comprises a means for causing a subspace sequestering means to become configured so as to sequester a sample in a subspace of said substantially enclosed space during entry and removal of a sample. This allows accessing a sample means for placing and maintaining a sample in a desired position and orientation, (ie. a sample supporting stage), with the benefit that only the sequestered subspace then needs substantial purging. The subspace sequestering means further enables reconfiguration to open the entire substantially enclosed space in the chamber to the sample, thereby facilitating its access thereof via UV range wavelength electromagnetic radiation.

The J.A. Woollam Co. VUV-VASE includes two-speed purge control means, such that a sequestered subspace can be purged, quickly, but when purging is substantially complete, a Nitrogen conserving slower maintenance purge speed can be effected. This is important as it provides a means of expense reduction via gas conservation.

A U.S. Pat. No. 6,813,026 to McAninch is disclosed as it describes a purge system for application in optical metrology tools. This Patent describes a system which, rather than purge a chamber in which a sample is present, includes means for flowing a gas over the surface of a sample at a location thereon at which an electromagnetic beam is caused to impinge. Present are an optics plate for supporting measurement optics and a movable stage. The lower surface of the optics plate is Claimed as bing planar in the 026 Patent. During use inert gas is injected between the lower planar surface of the optics plate and the upper surface of a sample. The gas flow also serves to clear the measurement area of the sample of absorbing species. It is noted that the gas flow is continuous during use and that no provision for conserving gas is provided.

Further, it is to be understood that causing a polarized beam of electromagnetic radiation to interact with a sample system generally causes change in the ratio of the intensities of orthogonal components thereof and/or the phase shift between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872,630 in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to account for phase shifts entered between orthogonal components of a beam of electromagnetic radiation, by system multiangle prisms and/or lenses.

Another Patent which is incorporated hereinto by reference is U.S. Pat. No. 5,969,818 to Johs et al. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair.

Another Patents incorporated hereinto by reference is U.S. Pat. No. 5,757,494 to Green et al., in which is taught a method for extending the range of Rotating Analyzer/Polarizer ellipsometer systems to allow measurement of DELTA'S near zero (0.0) and one-hundred-eighty (180) degrees. Said Patent describes the presence of a window-like variable bi-refringent component which is added to a Rotating Analyzer/Polarizer ellipsometer system, and the application thereof during data acquisition, to enable the identified capability.

A Patent to Thompson et al. U.S. Pat. No. 5,706,212 teaches a mathematical regression based double Fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to one another during data acquisition is described therein.

A Patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

A Patent to Finarov, U.S. Pat. No. 5,764,365 is disclosed as it describes a system for moving an ellipsometer beam over a large two-dimensional area on the surface of a sample system, which system utilizes beam deflectors.

A Patent to Berger et al., U.S. Pat. No. 5,343,293 describes an Ellipsometer which comprises prisms to direct an electromagnetic beam onto a sample system.

A Patent to Canino, U.S. Pat. No. 4,672,196 describes a system which allows rotating a sample system to control the angle of incidence of a beam of electromagnetic radiation thereonto. Multiple detectors are present to receive the resulting reflected beams.

A Patent to Bjork et al., U.S. Pat. No. 4,647,207 describes an ellipsometer system in which reflecting elements are moved into the path of a beam of electromagnetic radiation.

U.S. Pat. No. 6,081,334 to Grimbergen et al. describes a system for detecting semiconductor end point etching including a means for scanning a beam across the surface of a substrate.

A Patent to Ray, U.S. Pat. No. 5,410,409 describes a system for scanning a laser beam across a sample surface.

U.S. Pat. No. 3,874,797 to Kasai describes means for directing a beam of electromagnetic radiation onto the surface of a sample using totally internally reflecting prisms.

U.S. Pat. No. 5,412,473 to Rosencwaig et al., describes a ellipsometer system which simultaneously provides an electromagnetic beam at a sample surface at numerous angles of incidence thereto.

A Patent to Chen et al., U.S. Pat. No. 5,581,350 is identified as it describes the application of regression in calibration of ellipsometer systems.

An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration.

A paper by Nijs & Silfhout, titled "Systematic and Random Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (September 1994) describes first order corrections for imperfections in windows and compensators in Rotating Compensator ellipsometers.

Other papers of interest in the area by Azzam & Bashara include one titled "Unified Analysis of Ellipsometry Errors Due to Imperfect Components Cell-Window Birefringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al., titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

Also, a paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Further, Ellipsometry is generally well described in a great many number of publications, one such publication being a review paper by Collins, titled "Automatic Rotating Element Ellipsometers: Calibration, Operation and Real-Time Applications", Rev. Sci. Instrum, 61(8) (1990).

Even in view of the prior art, need remains for:
a material system investigation system which is functionally mounted to a three dimension location means for positioning said selected system at points in a three dimensional setting, including rotational capability;
a simple to use system for enabling easy sequential setting of different angle-of-incidence of a beam of electromagnetic radiation with respect to a surface of a sample system in ellipsometer, polarimeter, reflectometer, spectrophotometer and the like systems;
particularly where combined with an approach to account for any effects of the presence thereof, during evaluation of sample system PSI and DELTA values; and which system can further comprise purging means to enable investigating samples with electromagnetic radiation at wavelengths which are absorbed by, for instance, oxygen and water vapor present in the atmosphere.

SUMMARY OF THE INVENTION

A primary purpose and/or objective of the disclosed invention is to teach a system comprising a system selected from the group consisting of:
reflectometer;
rotating analyzer ellipsometer;
rotating polarizer ellipsometer;
rotating compensator ellipsometer;
modulation element ellipsometer;
Mueller Matrix measuring system;

functionally mounted to a three dimension location means for positioning said selected system at points in a three dimensional setting, including rotational capability to enable investigating any surface such as the inner or outer surface of a pipe.

Another primary purpose and/or objective of the disclosed invention is to teach a system for enabling easy sequential setting of different Angles-of-Incidence of a beam of electromagnetic radiation to a surface of a sample system, in material system investigation systems such as ellipsometers, polarimeters, reflectometers, spectrophotometers and the like systems.

Another purpose and/or objective of the disclosed invention is to describe regression based methodology for evaluating and compensating the effects of the presence electromagnetic beam intercepting angle-of-incidence changing systems, including where desired, parameterization of calibration parameters.

Yet another purpose and/or objective of the present invention is to provide a reflectometer, ellipsometer, polarimeter or the like system, which functionally comprises means for providing evacuation and/or gas near the surface of a sample while a beam of electromagnetic radiation is caused to be impinged thereupon.

It is another purpose and/or objective of the present invention to provide evacuation and/or a flow of gas via a mini-chamber which accesses at least a portion of said sample at which a beam of electromagnetic radiation is caused to be impinged thereupon.

It is yet another purpose and/or objective of the present invention to describe a method of use of the present invention system to investigate a sample with wavelengths which are relatively less absorbed by ambient atmospheric components during period in which gas is flowed over a sample surface, and which then to investigate a sample with wavelengths which are substantially absorbed by ambient atmospheric components during period in which at least a portion of the sample which is being investigated is contained in a formed "mini-chamber" which contains gas.

Other purposes and/or objectives of the present invention will become apparent upon a reading of the Disclosure and Claims.

DISCLOSURE OF THE INVENTION

The present invention is a system for positioning a source of a beam of electromagnetic radiation and a detector thereof in relation to a sample to be investigated comprising:
a source and detector of electromagnetic radiation and a sample;

which comprises means for effecting relative translational motion between said source and detector of electromagnetic radiation and said sample in three orthogonally related dimensions; and which comprises means for effecting rotational motion of said source and detector of electromagnetic radiation about at least one axis.

Said system can further comprise means for effecting rotational motion of said source and detector of electromagnetic radiation about at least one axis, comprises means for causing rotation about at least two orthogonally oriented axes and purging means to enable investigating samples with electromagnetic radiation at wavelengths which are absorbed by, for instance, oxygen and water vapor present in the atmosphere.

Said source and detector of electromagnetic radiation are typically mounted in fixed relationship to one another and preferably are comprised in a polarization state generator and a polarization state detector.

As did the disclosed invention in Parent application Ser. No. 11/105,852 filed Apr. 14, 2005, the presently disclosed invention breaks with conventional practice by teaching that the relative location between a Sample and a Source of Electromagnetic Radiation and a Data Detector in a Reflectometer or Ellipsometer and the like System should be accomplished by simultaneous motion of the Source of Electromagnetic Radiation and Data Detector, (eg. in Lab coordinates), while the Sample remains substantially fixed, (eg. in said Lab Coordinates). While, it is not beyond the scope of the present invention to provide a Stage which can be moved, such is not a focus of thereof. The presently disclosed invention further breaks with convention by teaching that means to produce a Beam of Electromagnetic Radiation, Set and Detect Polarization States thereof, and to direct motion in Three Dimensions should be mounted self contained "On-Board" a mobile system. That is, in a realized embodiment, the only required external connections are means to provide electrical power and means to carry data from said Data Detector to a Data Analysis System, and in advanced embodiments under development, battery power is also provided On-Board, and Data is transmitted via a wireless On-Board Transmitter.

The direct incentive for developing the presently disclosed invention is found in the desire of producers of "Samples" which are very large or of non-planar shapes, to be able to monitor many locations thereon. For instance, such a "Sample" might be a sheet of glass which has dimensions of Feet/Meters on a side, whereas conventionally "Samples" placed on Ellipsometer Stages are measured in on the order of inches/centimeters on a side. For the purpose of enabling monitoring many locations on very large Samples it is beneficial to have a Self-Contained "On-Board" Ellipsometer which mounts to a Two Dimensional locational system, (eg. an "X"-"Y" Plotter-like System), near the surface of said Large Sample, said Self Contained Ellipsometer System having the "On-Board" capability of directing Two Dimensional location in a plane parallel to the substantially flat surface of a monitored large sample, and distance, (eg. "Z"), offset from said Large Sample at set locations within the Two-Dimensional plane.

An example of an ellipsometer system suitable for use in the present invention is a spectroscopic rotating compensator material system investigation system comprising a source of an incoherent polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one Pseudo-Achromatic compensator(s) positioned at a location selected from the group consisting of:
  before said stage for supporting a material system;
  after said stage for supporting a material system; and
  both before and after said stage for supporting a material system.

Said ellipsometer system can further include means for flowing purge gas, such as Nitrogen, onto a region of a sample being investigated such that UV or IR wavelength electromagnetic radiation travels therethrough.

The disclosed invention system can further comprise means for enabling easy provision of multiple Angles-of-Incidence of a beam of electromagnetic radiation with respect to a sample system surface in material system investigation systems such as:
  ellipsometer;
  polarimeter;
  reflectometer; and
  spectrophotometer;
  Mueller Matrix measuring system;

which operate at least one wavelength in at least one wavelength range, such as:
  VUV;
  UV;
  Visible;
  Infrared;
  Far Infrared;
  Radio Wave.

In use, a disclosed invention electromagnetic beam intercepting angle-of-incidence changing system is situated near a sample system such that its functional effects can be easily entered into and removed from the path of an electromagnetic beam. When functionally in the path of the electromagnetic beam the disclosed invention system elements intercept electromagnetic beam radiation on both the impinging and reflected side of the sample system. When the disclosed invention electromagnetic beam intercepting angle-of-incidence changing system is caused to be functionally in the path of the electromagnetic beam it acts, via such as total internal reflection within multiangle prisms or functional equivalents, (eg. reflection from a sequence of mirrors), to direct said electromagnetic beam at the sample system at a different Angle-of-Incidence than is the case if the electromagnetic beam simply directly approaches and reflects from the sample system surface, however, and importantly as it is what provides the utility of the disclosed invention, the electromagnetic beam is directed to substantially the same spot, (eg. see the spot in FIGS. 10 and 11 at which the beam impinges on the Sample (SS)), on a sample system being investigated. That is, the same spot on a sample system surface is addressed regardless of the presence of a disclosed invention Angle-of-Incidence changing system in the pathway of the electromagnetic beam. Further, as the electromagnetic beam Locus beyond the disclosed invention Angle-of Incidence changing system is not changed by a disclosed invention Angle-of-Incidence changing system, the presence thereof in the path of an electromagnetic beam does not require any realignment of a Source of the electromagnetic beam, or Detector thereof. In addition, where a disclosed invention system is entered into the locus of an electromagnetic beam by physical motion, multiple disclosed invention electromagnetic beam intercepting angle-of-incidence changing systems can be present adjacent to one another such that each can, as desired by a user, be sequentially physically moved into place, and thereby provide the possibility of sequentially easily effecting multiple different Angles-of-Incidence. When multiple different disclosed invention Angle-of Incidence changing system(s) are utilized, they are distinguished by the presence of differently shaped Multiangle prisms, or functional equivalents thereof, therewithin. Note, however, that as is described later herein, some embodiments of the disclosed invention system are held stationary in position, and which electromagnetic beam enters a detector is controlled by shutter doors and/or control of the transmission/reflection properties of an internal surface of a multiangle prism.

In practical application, the disclosed invention can then include:
- at least one electromagnetic beam intercepting angle-of-incidence changing system which comprises elements that are easily functionally entered into the locus of the electromagnetic beam on both sides of a sample system;

in functional combination with:
- a material system investigation system comprising a source of electromagnetic radiation, a means for supporting a sample system, and a detector, such that in use a beam of electromagnetic radiation is provided by said source of electromagnetic radiation and is caused to reflect from a sample system placed on said means for supporting a sample system and enter said detector.

As mentioned, said at least one electromagnetic beam intercepting angle-of-incidence changing system, when caused to be functionally present in the path of an electromagnetic beam, serves to direct said electromagnetic beam onto substantially the same spot on the sample system as is the case where said at least one electromagnetic beam intercepting angle-of-incidence changing system is not so functionally present, but at an angle-of-incidence which is different than that which exists when said at least one electromagnetic beam intercepting angle-of-incidence changing system is not functionally present. Importantly, said at least one electromagnetic beam intercepting angle-of-incidence changing system does not effect, or require change of the locus of the electromagnetic beams outside said at least one electromagnetic beam intercepting angle-of-incidence changing system, on either side of said means for supporting a sample system, hence presently disclosed systems eliminate the requirement that a material system investigating system comprise multiple sources and/or detectors, or that the position of the source of electromagnetic radiation and/or detector thereof be changed during use to effect said electromagnetic beam angle-of-incidence change.

At least one electromagnetic beam intercepting angle-of-incidence changing system can comprise, present on each side of said means for supporting a sample system, at least one selection from the groups consisting of:
- multiple angle prism(s); and a system of mirrors;

said at least one electromagnetic beam intercepting angle-of-incidence changing system being slidably mounted to a guide element such that the functional presence thereof in the pathway of the locus of the electromagnetic beams on both sides of said means for supporting a sample system is effected by physical sliding motion of said at least one electromagnetic beam intercepting angle-of-incidence changing system along said guide element.

Another embodiment of the disclosed invention system provides that at least one electromagnetic beam intercepting angle-of-incidence changing system comprises:
- a first multiangle prism on the incident side of said means for supporting a sample system and a second multiangle prism thereafter, said first and second multiangle prisms each having a first and a second side, each said multiangle prism presenting with first and second inner surfaces at said first and second sides respectively.

In this embodiment, the first and second sides of each multiangle prism have means for changing the properties of inner surface thereof from essentially transmissive to essentially reflective. Said means can be, for instance a voltage controlled liquid crystal array. In use, each multiangle prism is oriented such that an electromagnetic beam entering thereinto encounters said first or second inner surface thereof and either passes therethrough and progresses on to contact a sample system placed on said means for supporting a sample system; or reflects from said first or second inner surface thereof and then from said second or first inner surface thereof, respectively, and then progresses on to contact a sample system placed on said means for supporting a sample system. Said material system investigating system can further comprise at least one shutter door which can be opened to let the electromagnetic beam pass, or closed to block its passage, said at least one shutter door being positioned in the electromagnetic beam locus selected from the group consisting of:
- defined by transmission through said first or second side of said first multiangle prism; and
- defined by reflection from said first or second side of said first multiangle prism;

said at least one shutter door being positioned between a first multiangle prism and the means for supporting a sample system and/or between said means for supporting a sample system and a second multiangle prism.

Another embodiment of a disclosed invention material system investigating system provides that at least one electromagnetic beam intercepting angle-of-incidence changing system comprises:
- on first and second sides of said means for supporting a sample system, first and second, respectively, beam splitters.

Said first and second beam splitters each have the property that they pass approximately half, and reflect approximately half of a beam of electromagnetic radiation caused to be incident thereupon at an oblique angle to a surface thereof. Said at least one electromagnetic beam intercepting angle-of-incidence changing system further comprises a first reflective means positioned to intercept the approximately half of the electromagnetic beam which reflects from said first beam splitter on the incident side of said means for supporting a sample system and direct it toward said means for supporting a sample system. Also present is a second reflective means positioned after said means for supporting a sample system to intercept an electromagnetic beam which reflects from a sample system placed on said means for supporting a sample system and direct it toward the second beam splitter. Said material system investigating system further comprises at least one shutter door which can be opened to let the electromagnetic beam pass, or closed to block its passage, said at least one shutter door being positioned in the pathway of the electromagnetic beam between which progresses along a locus selected from the group consisting of:
- defined by passage through said first beam splitter; and
- defined by reflection from said first beam splitter;

on either side of said means for supporting a sample system. Typically four shutter doors will be present, two on each side of the means for supporting a sample system, said shutter doors being positioned in the loci of the electromagnetic beams which are most easily identified as those transmitting through and reflecting from the beam splitter on the incident side of the means for supporting a sample system, although said beams are continuous past sample system from which they reflect.

The material system investigating system including the disclosed invention can also include means for adjusting the orientation of at least one angle-of-incidence changing element in an electromagnetic beam intercepting angle-of-incidence changing system, optionally in simultaneous combination with included lenses positioned to focus a beam of electromagnetic radiation onto a sample system.

Continuing, as taught in U.S. Pat. No. 5,969,818 to Johs et al., (which is incorporated herein by reference), the disclosed invention at least one electromagnetic beam intercepting angle-of-incidence changing system can comprise, on first and/or second sides of said means for supporting a sample system, at least one system of mirrors, said at least one system of mirrors being comprised of:

a means for changing the propagation direction of an initial beam of electromagnetic radiation without significantly changing the phase angle between orthogonal components thereof, said means comprising two pairs of reflecting mirrors oriented so that said initial beam of electromagnetic radiation reflects from a first reflecting means in the first pair of reflecting means to a second reflecting means in said first pair of reflecting means, in a first plane; and such that the beam of electromagnetic radiation which reflects from the second reflecting means in said first pair of reflecting means reflects from the first reflecting means in said second pair of reflecting means to said second reflecting means in said second pair of reflecting means, in a second plane which is essentially orthogonal to said first plane; such that the direction of propagation of the beam of electromagnetic radiation reflected from the second reflecting means in said second pair of reflecting means is different from the propagation direction of the initial beam of electromagnetic radiation; the basis of operation being that changes entered between the orthogonal components by the first pair of reflective means is canceled by that entered by the second pair of reflective means.

It should be appreciated then that the disclosed invention is found primarily in the addition of disclosed invention Angle-of-Incidence changing system(s) to conventional material system investigation systems, and that the entering and/or removing procedure can be via physical motion of an angle-of-incidence changing system into and out of the locus of a beam of electromagnetic radiation, by operation of shutter doors statically placed in the locus of a beam of electromagnetic radiation, or by altering the properties of the inner surface of a multiangle prism statically placed to intercept a beam of electromagnetic radiation, to be transmissive or reflective. In any embodiment thereof, the utility of the disclosed invention is based upon the ease with which an angle-of-incidence of a beam of electromagnetic radiation to the surface of a sample system can be changed, (ie. typically attendant requirement for changing the position of a source and/or detector of electromagnetic radiation is not required).

The disclosed invention then comprises the Mounting of a material system investigation system such as Ellipsometer, Polarimeter, Reflectometer or Spectrophotometer System, (with or without a disclosed invention angle-of-incidence changing system present), on an X-Y-Z Position Control System so it can be moved around the surface of a large area Sample, (Z is for focus). While non-limiting, an example is that very large, (eg. multiple feet by multiple feet), slabs of glass are these days coated with Indium-Tin-Oxide. It is necessary to "Map" the sample system to determine if the (ITO) thickness is even over its area. A solution is to place an Ellipsometer on a system that allows it to be moved in X-Y-Z directions, then sequentially move it, and take data, and repeat. (Note that if an Ellipsometer or Polarimeter or Reflectometer System is mounted to move in an X-Z or Y-Z plane, instead of the X-Y plane, then the Y or X, respectively, direction is for focus).

Further, it is to be understood that the disclosed invention incorporates by reference the regression based calibration methodology of U.S. Pat. No. 5,872,630 into its operation to simultaneously evaluate sample system characterizing parameters such as PSI and DELTA, as well as Ellipsometer or the like and disclosed invention system characterizing parameters, and also incorporates by reference the Window Correction and correlation breaking methodology of U.S. Pat. No. 6,034,777 to account for phase shifts entered between orthogonal components of a beam of electromagnetic radiation, by disclosed invention system multiangle prisms, system of mirrors and optional lenses, or functional equivalents.

Again, disclosed invention angle-of-incidence changing systems can be used in Polarimeter, Reflectometer, Spectrophotometer and the like Systems, as well as in Ellipsometer Systems, whether monochromatic or over a spectroscopic wavelength range.

To aid with Disclosure as to how the disclosed invention can be practiced, relevant material from U.S. Pat. Nos. 5,872, 630 and 6,034,777 is included directly herewithin. In particular, while not limiting, a relevant ellipsometer system to which the disclosed invention system can be described as comprising:

a. a Source of a beam of electromagnetic radiation;
    b. a Polarizer element;
    c. optionally a compensator element;
    d. (additional element(s));
    e. a sample system;
    f. (additional element(s));
    g. optionally a compensator element;
    h. an Analyzer element; and
    i. a Detector System;

wherein, in the context of the disclosed invention, said additional component(s) in d. and f. each comprise at least one electromagnetic beam intercepting angle-of-incidence changing system element which can be easily entered into the locus of the electromagnetic beam on both sides of said sample system, which at least one electromagnetic beam intercepting angle-of-incidence changing system elements serves to direct said electromagnetic beam onto substantially the same spot on the sample system as is the case where the said at least one electromagnetic beam intercepting angle-of-incidence changing system elements are not present, but at an angle-of-incidence which is different than that when said at least one electromagnetic beam intercepting angle-of-incidence changing system is not present. Said at least one electromagnetic beam intercepting angle-of-incidence changing system elements does not effect, or requiring change of, the locus of the electromagnetic beams outside said at least one electromagnetic beam intercepting angle-of-incidence changing system elements, on either side of a sample system, hence does not require change of position of the source of electromagnetic radiation and/or detector to effect change said angle-of-incidence. The sample system investigation system electromagnetic beam intercepting angle-of-incidence changing system can comprise multiangle prisms and/or plurality of mirrors, and/or shutter doors and/or means for changing the characteristics of the internal surface of a multiangle prism etc.

Continuing, under the teachings of the 630 Patent, each of said components b.-i. of the ellipsometer system must be accurately represented by a mathematical model, along with a vector which represents a beam of electromagnetic radiation provided from said source of a beam electromagnetic radiation identified in a. above.

It is noted that various ellipsometer configurations provide that a Polarizer or Analyzer or Compensator(s) can be rotated during data acquisition, and are describe variously as Rotating Polarizer (RPE), Rotating Analyzer (RAE) and Rotating Compensator (RCE) Ellipsometer Systems.

The disclosed invention system then, is applied in a material system investigating system, (eg. ellipsometer; polarimeter; reflectometer; spectrophotometer or the like, operating in, for instance, a VUV, UV, Visible, Infrared, Far Infrared or Radio Wavelength range, and comprises a source of electromagnetic radiation, a means for supporting a sample system, and a detector, such that in use a beam of electromagnetic radiation is provided by said source of electromagnetic radiation and is caused to reflect from a sample system placed on said means for supporting a sample system and enter said detector, at an angle-of-incidence which can be set by said disclosed invention angle-of-incidence changing system.

The at least one electromagnetic beam intercepting angle-of-incidence changing system can comprise a selection from the group consisting of:
  multiple angle prism(s);
  multiple angle prism(s) including means for changing the characteristics of internal surfaces thereof;
  a system of mirrors;
  shutter doors;

on each side of said sample system.

As mentioned, the material system investigating system can be mounted to an X-Y-Z position control system and can be oriented to investigate a surface of a sample oriented in a horizontal or vertical or a plane thereinbetween.

A disclosed invention material system investigating system can include at least two multiple angle prisms at a location on at least one of said both sides of said sample system, and can include Lenses positioned to focus a beam of electromagnetic radiation onto a sample system. There can also be present means for adjusting the orientation of at least one multiangle prism, or functional equivalent, in a angle-of-incidence changing system, said means allowing adjusting the orientation of at least one lens alone or in fixed combination with an electromagnetic beam intercepting angle-of-incidence changing system multiangle prism or functional equivalent.

Another, purely mechanical, system for setting the angle of incidence of a beam of electromagnetic radiation comprises, as viewed in elevation, first and second arms pivotally interconnected to one another at an upper aspect thereof by a first pivot means, said first and second arms projecting downward and to the left and right of said first pivot means. Distal ends of said first and second arms are pivotally affixed to third and forth arms, said third and forth arms being pivotally interconnected to one another at a lower aspect thereof and said third and forth arms being projected upward and to the left and right of said pivotal interconnection at said lower aspect thereof, respectively. There are at least two pivotally affixed substantially downward projecting arms attached to each of said third and forth arms, distal ends of which are pivotally affixed to fifth and sixth arms which are not interconnected to one another, but project upward to the left and right, respectively. Affixed to one of said fifth and sixth arms is a source of a beam of electromagnetic radiation, and to the other of said sixth and fifth arms a detector of said beam of electromagnetic radiation is affixed. There is further a sample located such that a beam of electromagnetic radiation produced by said source of a beam of electromagnetic radiation reflects from an upper surface of said sample and enters said detector of said beam of electromagnetic radiation. In use when the first pivot means at which said first and second arms are interconnected is caused to be vertically raised or lowered, the angle of incidence at which the beam of electric radiation approaches said sample surface is changed, but the location at which it interacts with said sample surface remains substantially unchanged.

As already mentioned, the material system investigating system can be applied in a setting selected from the group consisting of:
  in-situ; and
  ex-situ.

Continuing, as mentioned in the Background Section, Ultraviolet (UV), Vacuum Ultraviolet (VUV) Infra-Red (IR) or Near Infrared (NIR) Wavelengths are absorbed by oxygen or water vapor, hence where they are applied to a sample by a Reflectometer, Ellipsometer, Polarimeter or the like System, it is necessary to evacuate and/or purge at least the region around a sample, and preferably along the pathway of the electromagnetic radiation from the source thereof, to a detector thereof.

With the foregoing in mind, it is disclosed that the present invention can comprise a:
  reflectometer;
  ellipsometer;
  spectroscopic ellipsometer;
  polarimeter; or
  spectroscopic polarimeter;
  Mueller Matrix measuring system;

system for investigating a sample with electromagnetic radiation comprising:
  a source of electromagnetic radiation and a detector of electromagnetic radiation oriented such that in use said source of electromagnetic radiation provides a beam of electromagnetic radiation at an angle of incidence to a surface of a sample, and said detector of electromagnetic radiation receives a resulting beam of electromagnetic radiation reflected therefrom.

As already disclosed said source and detector of electromagnetic radiation are functionally mounted to a common placement means, and said sample is present on a separate stage. The system further comprises means for causing relative motion between said source and detector of electromagnetic radiation as a unit, and said sample. Said system further comprises interface means for providing slidable contact or substantial slidable contact between said common placement means and said separate stage such that a mini-chamber which accesses said sample is formed thereby. Said system further comprising means for introducing gas into said mini-chamber and means for displaying data provided by the detector of electromagnetic radiation.

The present invention system can comprise an ellipsometer or polarimeter system for analyzing sample systems using electromagnetic radiation with wavelengths in the ultraviolet, vacuum ultraviolet, infrared or near infrared wavelength range, said ellipsometer system comprising a mini-chamber which accesses at least a portion of a sample; said ellipsometer or polarimeter system further comprising:
  a) source means for providing of a beam including ultraviolet, vacuum ultraviolet, infrared or near infrared wavelength range electromagnetic radiation;

b) polarization state setting means for setting a polarization state in at least a selected range of wavelengths in a beam including ultraviolet, vacuum ultraviolet, infrared or near infrared wavelength range electromagnetic radiation;

c) a means for placing and maintaining a sample system in a desired position and orientation, said means for placing and maintaining a sample system in a desired position and orientation such that at least a portion of a sample can be sequestered by said mini-chamber;

d) data detector means for receiving an electromagnetic beam which is caused to interact with a sample which is secured in place by said means for placing and maintaining a sample system in a desired position and orientation;

e) computer means for analyzing at least some data provided by said data detector means for receiving an electromagnetic beam after it interacts with said sample and/or storing at least some of said data and/or an analyzed version thereof in machine readable media and/or displaying at least some of said data and/or an analyzed version thereof electronically or by non-electronic means, and/or causing at least some of said data and/or an analyzed version thereof to be represented by a signal which is applied to provide a concrete and tangible result.

As mentioned, the present invention can be applied at wavelengths which are absorbed by oxygen and water vapor and provides that said source means and polarization state setting means, polarization state detecting means and data detector means are all functionally associated with a common placement means which can be positioned to slidably contact or substantially slidably contact said means for placing and maintaining a sample system in a desired position and orientation via interface means. When actual or substantial slidable contact is effected therebetween a mini-chamber is formed between said common placement means and said means for placing and maintaining a sample system in a desired position and orientation, said mini-chamber accesses at least a part of said sample. Said common placement means can be of single or multiple piece construction. Said mini-chamber further has means functionally affixed thereto for effecting evacuation and/or entering purging gas into said mini-chamber. In use a sample is caused to be positioned and oriented by said means for placing and maintaining a sample in a desired position and orientation, and actual or substantial slidable contact is realized between said common placement means and said means for placing and maintaining a sample in a desired position and orientation, via said interface means. Purging gas is then caused to be entered into said mini-chamber, and said source means for providing of a beam including ultraviolet, vacuum ultraviolet, infrared or near infrared wavelength range electromagnetic radiation is caused to provide a beam including ultraviolet vacuum ultraviolet, infrared and/or near infrared wave lengths. Said polarization state setting means for setting a polarization state in a selected range of wavelengths in a beam including electromagnetic radiation is caused to impose a polarization state thereupon and said resulting beam of electromagnetic radiation is caused to reflect from said sample and enter said data detector. Said computer means is then applied to analyze data provided by said data detector and display it and/or an analyzed version thereof, and/or store at least some of said data and/or an analyzed version thereof in machine readable media, and/or causing at least some of said data and/or an analyzed version thereof to be represented by a signal which is applied to provide a concrete and tangible result.

It is again noted that an ellipsometer or polarimeter can be considered to comprise a Polarization State Generator, (which comprises a source of electromagnetic radiation and a means for imposing a polarization state thereupon, a Stage for supporting a Sample, and a Polarization State Detector which comprises a polarization state analyzer and a data detector. The present invention system can then be recited as an ellipsometer or polarimeter comprising sequentially, a polarization state generator, a stage for supporting a sample and a polarization state detector, wherein said polarization state generator and polarization state detector are functionally associated with a common placement means which can be positioned to slidably contact or substantially contact said stage via interface means. When said slidable contact is effected a mini-chamber is formed between said common placement means and said stage with said mini-chamber accessing at least a part of a surface of said sample. Said mini-chamber further has means functionally affixed thereto for effecting evacuation and/or entering purging gas into said mini-chamber such that in use a sample is caused to be positioned on said stage and actual or substantial slidable contact realized between said common placement means and said stage via said interface means. Then purging gas is caused to be entered into said mini-chamber, and said polarization state generator is caused to provide a beam electromagnetic radiation which is directed to reflect from said sample and enter said data detector; said computer means is applied to analyze data provided by said data detector, and said data per se. or results of analysis thereof can be displayed and/or stored and or used to form a signal representing it.

An improvement provided by the present invention is a means for providing gas sequestered in a formed "mini-chamber" in the vicinity of a location on a surface of a sample during investigation thereof by electromagnetic radiation. While similar in purpose to the system described in U.S. Pat. No. 6,813,026 to McAninch, (the system of which can be applied in the present invention), taking guide from the J.A. Woollam VUV system described briefly in the Background Section, which provides a reduced gas flow mode, the present invention does not necessarily require a continuous flow of gas during use. Rather, the present invention system can provide means for forming a "mini-chamber" which accesses therewithin at least a portion of a sample. The method of use of the present invention can involve a period of flowing gas over a sample surface to, for instance, remove debris, but then there is formed a gas conserving "mini-chamber" which accesses at least a portion of said sample. Investigation of said sample with electromagnetic radiation comprising wavelengths in, for instance, the IR and/or UV and VUV ranges, which wavelengths are absorbed by ambient atmospheric component such as oxygen and water vapor, is then performed. It is noted that data pertaining to wavelengths not absorbed by Oxygen and/or Water Vapor can be obtained during an evacuation and/or purging procedure before said procedure is completed. This structured data collection approach allows an efficient use of time.

A method enabled by the present invention involves analyzing sample with spectroscopic electromagnetic radiation comprised of wavelengths which are absorbed by oxygen and/or water vapor comprises the steps of:

in any functional order practicing steps a, a' and a":

a) providing a system for forming a mini-chamber which encloses a substantially enclosed space which accesses at least a portion of a sample, to which mini-chamber is functionally affixed a means for evacuating or purging said substantially enclosed space of oxygen and/or water vapor, and means for entering a beam of electromagnetic radiation thereinto, and a means for exiting electromagnetic radiation therefrom; and a') providing a source of a spectroscopic beam electromagnetic radiation comprised of wavelengths which are absorbed by oxygen and/or water vapor and wavelengths which are not absorbed by oxygen and/or water vapor; and a") providing a data detector of spectroscopic electromagnetic radiation and means for displaying detected data.

Said method then proceeds with practice of steps b and c:

b) positioning a sample in said system for forming a mini-chamber which encloses a substantially enclosed space which accesses at least a portion of a sample;

c) causing said means for evacuating or purging said substantially enclosed space of oxygen and/or water vapor to tangibly and concretely evacuate or purge said substantially enclosed space of oxygen and/or water vapor, and causing said source of a spectroscopic beam electromagnetic radiation comprised of wavelengths which are absorbed by oxygen and/or water vapor to provide a beam of said electromagnetic radiation comprised of wavelengths which are absorbed by oxygen and/or water vapor to enter said means for entering a beam of electromagnetic radiation along a locus, such that it interacts with said sample, reflects therefrom, and exits said means for exiting electromagnetic radiation and enters said detector of spectroscopic electromagnetic radiation. The result is that when said substantially enclosed space is sufficiently evacuated or purged of oxygen and/or water vapor, data is provided by said data detector for wavelengths which are absorbed by oxygen and/or water vapor.

A modified method of investigating a sample with spectroscopic electromagnetic radiation comprised of wavelengths which are absorbed by oxygen and/or water vapor and wavelengths which are not absorbed by oxygen and/or water vapor, comprises a modified procedure wherein during the evacuation or purging process, while oxygen and/or water vapor is still present in said substantially enclosed space in sufficient quantity to absorb said wavelengths which are absorbed by said oxygen and/or water vapor, data is provided by said data detector for wavelengths which are not absorbed by oxygen and/or water vapor, and such that once said substantially enclosed space is sufficiently evacuated or purged of oxygen and/or water vapor, data is provided by said data detector for wavelengths which are absorbed by oxygen and/or water vapor.

The foregoing methods can then involve performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

The disclosed invention will be better understood by reference to the Detailed Description Section of this Specification, in coordination with the Drawings.

BRIEF DESCRIPTION OF THE DRAWINGS

FIGS. 1c and 1d show function enhancing embodiments of the present invention which allow rotational capability.

FIG. 8 shows demonstrates a present invention ellipsometer system situated on "X"-"Y" control means above a large sample.

FIG. 9a demonstrates a present invention ellipsometer system situated on "X"-"Y" control means above a large sample, including a system for flowing purging gas onto a sample.

FIG. 9i shows that a region (T) which is transparent to applicable wavelengths is present.

FIG. 13 shows Multiangle Prisms (MAP) comprise a disclosed invention electromagnetic beam intercepting angle-of-incidence changing system on right and left sides thereof.

FIG. 14a shows how a Multiangle Prism (MAP) changes the pathway of an Electromagnetic Beam by Total Internal Reflection therewithin.

FIG. 14b shows how a plurality of Mirrors can change the pathway of an Electromagnetic Beam by Reflection therefrom.

FIG. 15 shows a side elevational view of an adjustable mounting means for a Multiangle Prism (MAP), and optionally an Optical Lens (OL).

DETAILED DESCRIPTION

Figure 1A:
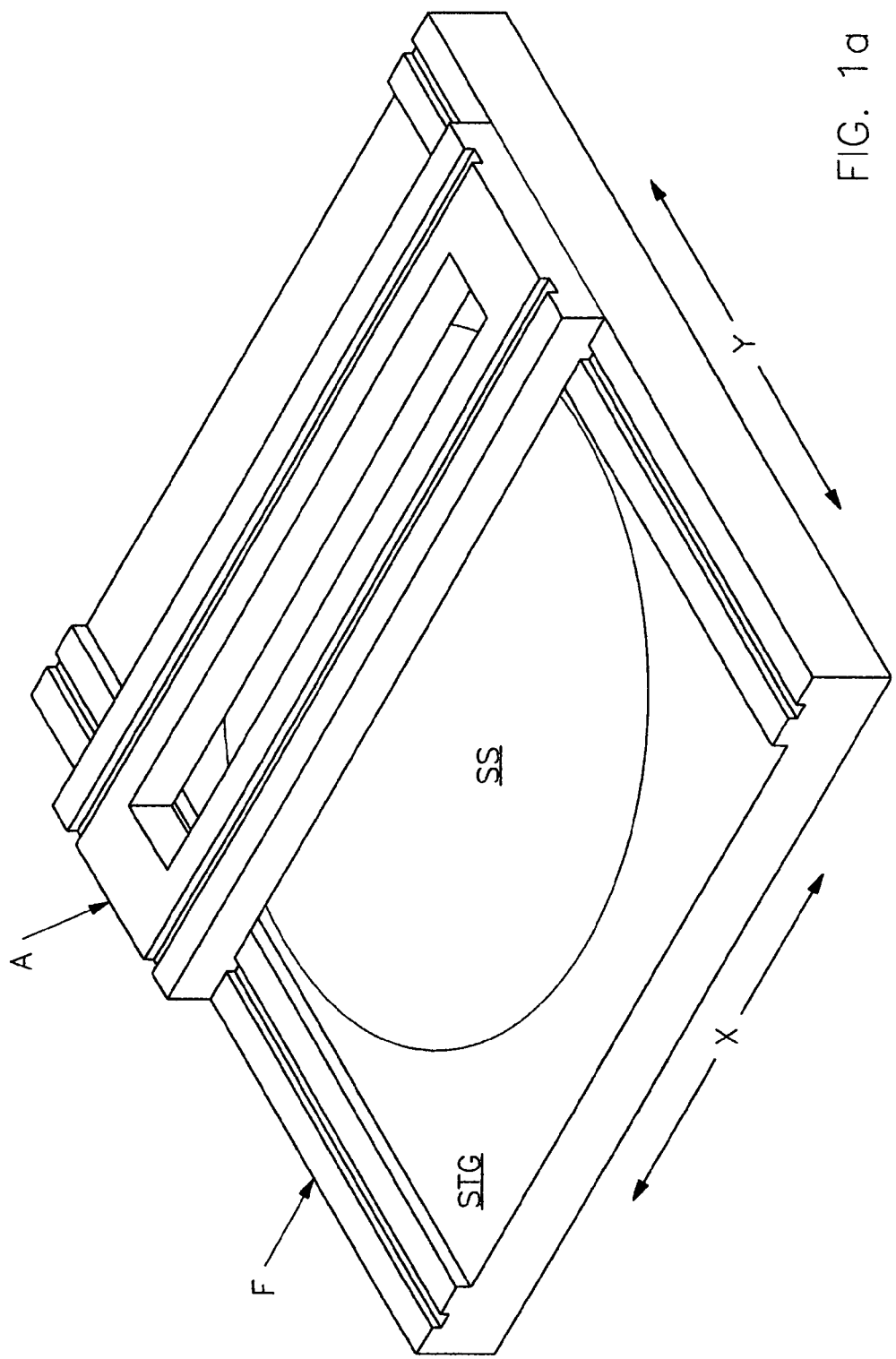
FIG. 1a demonstrates a perspective view of a Stage (STG) for supporting a Sample (S), said Stage (STG) being being functionally combined with a Frame (F) which allows Frame (A) to move atop thereof.
Figure 1B:
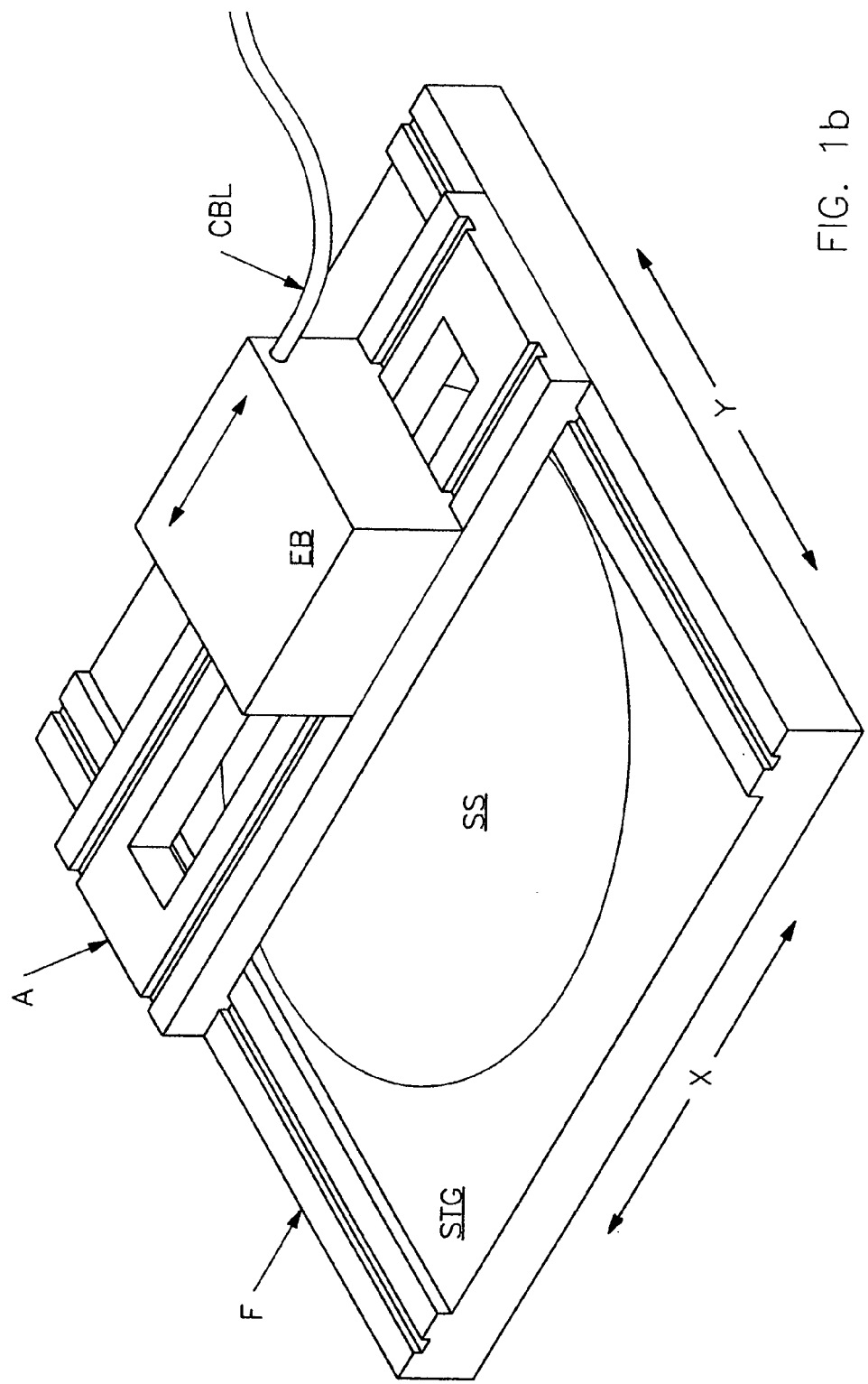
FIG. 1b demonstrates addition of Black Box (E) atop Frame (A), said Black Box (F) being movable atop Frame (A).

As disclosed in Parent application Ser. No. 11/105,852, FIGS. 1a and 1b demonstrate, in FIG. 1a, a perspective view of a Stage (STG) for supporting a large Sample (S), (eg. on the order of Feet/Meters in diameter), said Stage (STG) being being functionally combined with a Frame (F) which allows a Frame (A) to move atop thereof in a (Y) direction. Note that Frame (A) has an open middle region through which a Beam (E) of electromagnetic radiation, (for example see FIG. 2), can pass to reach the Sample (SS). FIG. 1b demonstrates addition of Black Box (EB) atop Frame (A), said Black Box (EB) being movable in an (X) direction atop Frame (A). (Note, while FIGS. 1a and 1b show that Sample facing upward, this does not limit application to a configuration wherein the shown system is rotated so that the sample faces laterally or is oriented in any other plane). While Also shown is an optional Cable (CBL) which can serve to provide electrical power into, and carry Data Detector Signals to external Analysis means. The disclosed invention can, however, include "on-board" battery power sources, and/or wireless data transmission means for providing data to external analysis means. It is mentioned that while not shown, motion of the Black Box (EB) can be caused by any functional means. For instance, a motor/gear arrangement or where functional a motor/rubber wheel etc. can be applied between the Black Box (EB) and Frame (A), and between Frame (A) and Frame (F), as well as between Frame (C) and Frame (D) (see FIG. 2). A functional motor can be a computer driven "Stepper Motor". It is also noted that the system in FIGS. 1a and 1b can be rotated so that in laboratory coordinates Frame (A) projects vertically, and remain within the description. In that case the (X-Y) plane should be considered to be project upward and into/out of the paper.

FIG. 1c shows a present invention function demonstrating embodiment of the present invention. Shown are a Frame (F) having a Horizontally Oriented Track (HT) therein. Horizontally, slidably supported in said Horizontally Oriented Track (HT) is a Base (B) Element which comprises a Vertically Oriented Track (VT) therein. Vertically slidably supported in said Vertically Oriented Track (VT) is a Head (H) Element. Said Head Element comprises Polarization State Generation (PSG) and Polarization State Detector (PSD) means, and Camera and Proximity Detecting Means (CaPr). Also shown is a Sample (SS) which presents with an irregular Outer Surface (OS) topology. In use said Base (B) Element can be caused to move horizontally in said Horizontally Oriented Track (HT), or said Sample (SS) can be moved to the Left or Right in FIG. 1c to position a location on the Sample (SS) Outer SUrface (OS) where desired. As well said Polarization State Generation (PSG) means can be applied to provide a beam of electromagnetic radiation (Ab) to said Sample (SS), such that it interacts therewith and reflects into said Polarization State Detector (PSD). Simultaneously said Camera and Proximity Detecting Means (CaPr) can be applied to provide insight to the visual appearance of the Sample (SS) at the location at which the beam of electromagnetic radiation (Ab) impinges on said Sample (SS), and to provide an indication of proximity of the Head (H) to said Sample (SS) Outer Surface (OS). Note that indication of the Camera area of coverage is provided by the lines (Cb), and a beam from and to the Proximity Detector (PR) is indicated by (Prb). The present invention can apply the Proximity Detector (Pr) to, for instance, override other controls when the Head (H) is coming dangerously close to the Outer Surface (OS) of the Sample via vertical motion at a location above said Sample (SS), or via horizontal motion along the irregular topology of the Sample (SS) Outer Surface (OS). Note that indication of a Motor (M) which can provide rotational $Rot_{ER}$ motion of said Head (H) about Extension Rod (ER). Such can be useful here a Sample (SS) has a Curved Outer Surface (OS) region, such as indicated by (CC) for instance. In addition note the Frame (F) can be subjected to a Rotation $Rot_F$ to allow, for instance, positioning a Beam (Ab) in the curved location between Region 1 and Region 2. Of course functional equivalent means for providing the various described motions, (eg. Pipe (P) motions), can be substituted and the system remain within the scope of the combination presented.

FIG. 1d, there is shown a variation of the embodiment of FIG. 1c. Note that the Base (B) supports a Motor (M) which can be moved Vertically or Horizontally via motion in the Frame (F) Vertical (VT) and Horizontal (HT) Tracks. The Extension Rod (ER) is attached at its distal end to the Head (H), which again comprises Polarization State Generation (PSG) and Polarization State Detector (PSD) means, and Camera and Proximity Detecting Means (CaPr). In the FIG. 1d embodiment, said Head (H) is shown as inserted into a Pipe (P) having an Inner Surface (IS), investigation of which it is desired via a beam of electromagnetic radiation (Ab). The region of the Inner Surface (IS) of said Pipe (P) which the Camera Means (Ca) can monitor is agains indicates by lines (Cab), and the Proximity Detector (PR) is again shown to provide a Beam (Pr) which is used to monitor proximity of the Head (H) to said Inner Surface (IS). Operation is similar to that of the embodiment shown in FIG. 1c. It is noted that while the Motor (M) in FIG. 1d is shown affixed to said Base (B) it could be afixed to the Frame (F) as in FIG. 1c, and vice-versa. Note also that the Motor (M) can be subjected to back and forward motion via Support (S) in YBase (Yb). Again, functional equivalents for effecting the various motions, (eg. Sample (SS) motion), can be substituted and the combination of elements remain within the scope of the present invention. It is noted that the Sample (SS) in FIG. 1c can be interpreted as being the outer surface of a pipe.

Figure 3:
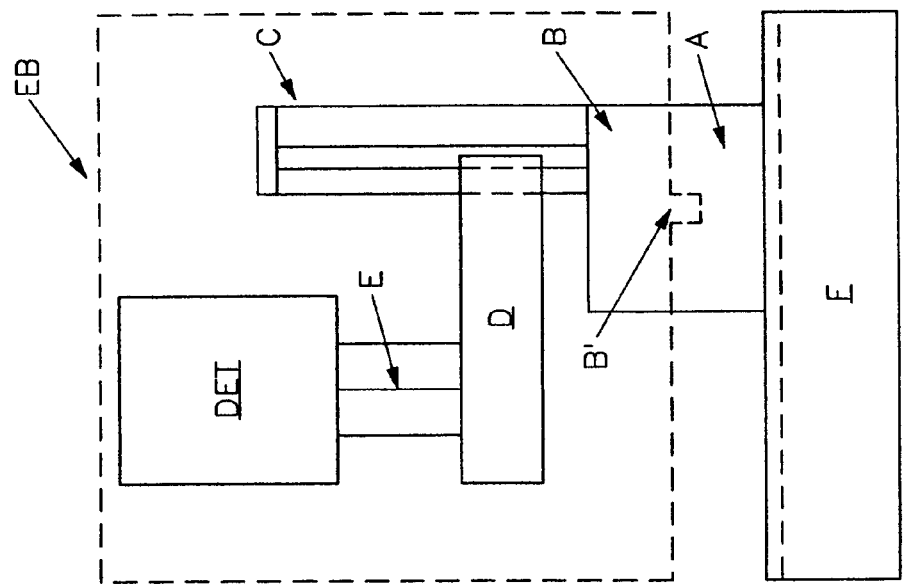
FIGS. 2 and 3 demonstrate in Frontal and Side elevation that the contents of the Black Box (E) can comprise Ellipsometer, Polarimiter, Reflectometer, Spectrophotometer, Mueller Matrix Measuring and the like systems which comprise a Source (LS) and Detector (DET) of electromagnetic radiation.
Figure 2:
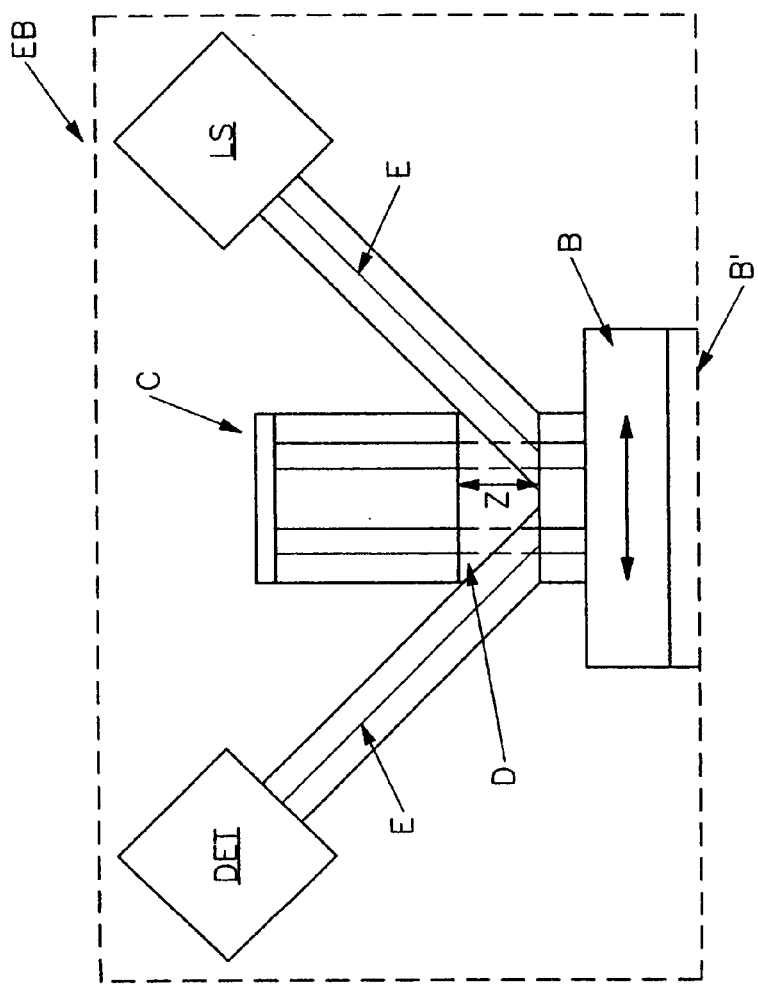

FIGS. 2 and 3 demonstrate in Frontal and Side elevation that the contents of the Black Box (EB) can comprise Ellipsometer, Polarimiter, Reflectometer, Spectrophotometer, Mueller Matrix Measuring and the like systems which comprise a Source (LS) and Detector (DET) of electromagnetic radiation. Note the indication of possible movement of element (D), to which said Source (LS) and Detector (DET) are shown affixed, in the (Z) direction.

In use a Large Sample (S) is placed on the Stage (STG) with its upper surface oriented parallel to the plane formed by "X" and "Y" in FIG. 1a. Control Means (C) directs the positioning of the System (SYS) at a series of "X" "Y" and "Z" positions, whereat said positions Sample (S) investigation is desired to be conducted by causing said Source (LS) to provide a beam of Electromagnetic Radiation and direct it at an obliques angle onto the Upper Surface of said Sample, with reflected Electromagnetic radiation being entered into said Data Detector (DET).

(Note, the actual (X), (Y) and (Z) effecting motion means are not shown, but can comprise any functional motion causing means means, including Computer controlled Stepper Motors, as can rotational motions).

Figure 4:
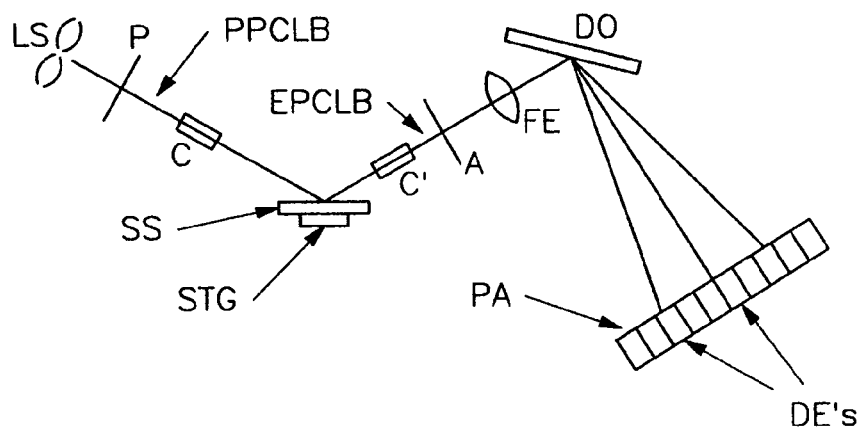
FIG. 4 shows a generalized Ellipsometer System.

FIG. 4 shows a generalized Ellipsometer System. Shown are a Source of Electromagnetic Radiation (LS), a Polarizer (P), a Compensator (C), a Sample (MS) on a Sample Supporting Stage (STC), a Compensator (C') a Focusing Lens (FE) a Dispersive Optics (D) and a Multi-Element Detector System. Removal of (P), (C), (C') and (A) provides the general configuration of a Reflectometer. The Focusing Optics can in some systems be eliminated. Said system can be operated as Rotating Polarizer (P), Rotating Analyzer (A) or Rotating Compensator (C) and/or (C') during data collection. For the purposes of this Disclosure, it is also to be understood that what is identified as a Compensator (C) (C') could be a Modulation Element, (eg. electro-optic or magneto-optic etc.), with the result being a Modulation Element Ellipsometer. Other than as might be specified by Claims, it is not the specific Reflectometer or Ellipsometer type which distinguishes the present invention.

Figure 5:
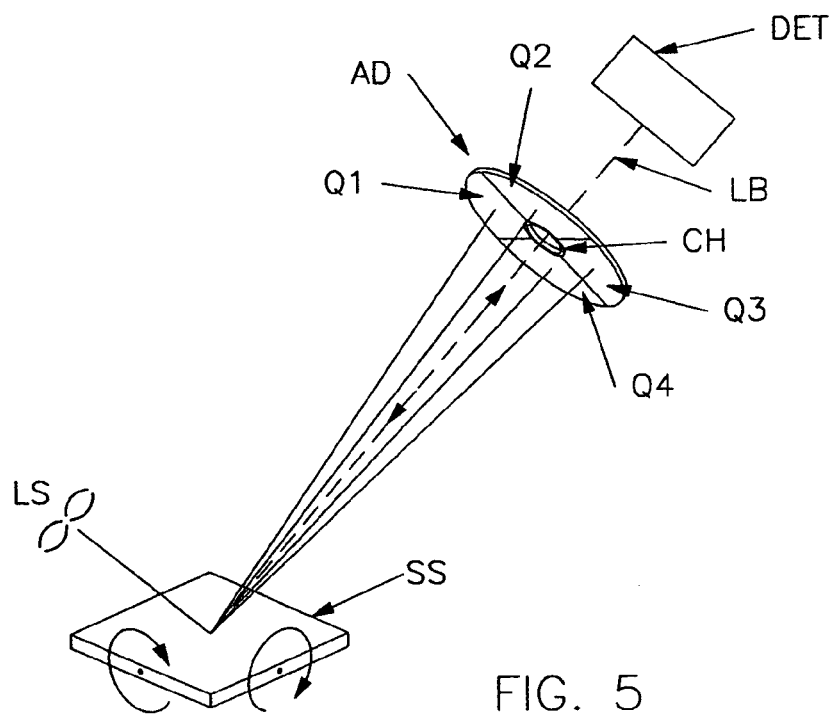
FIG. 5 shows application of a Multi-Element Detector to align a Sample.
Figure 6:
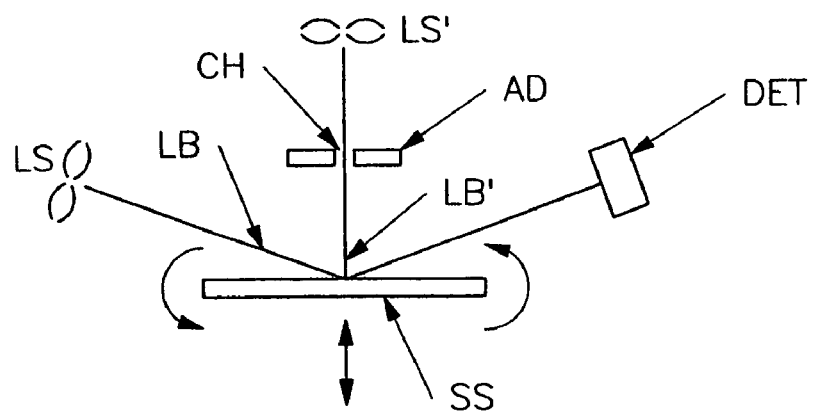
FIG. 6 shows a system which can be applied to provide a signal allowing "X" and "Y" plane adjustment.
Figure 7:
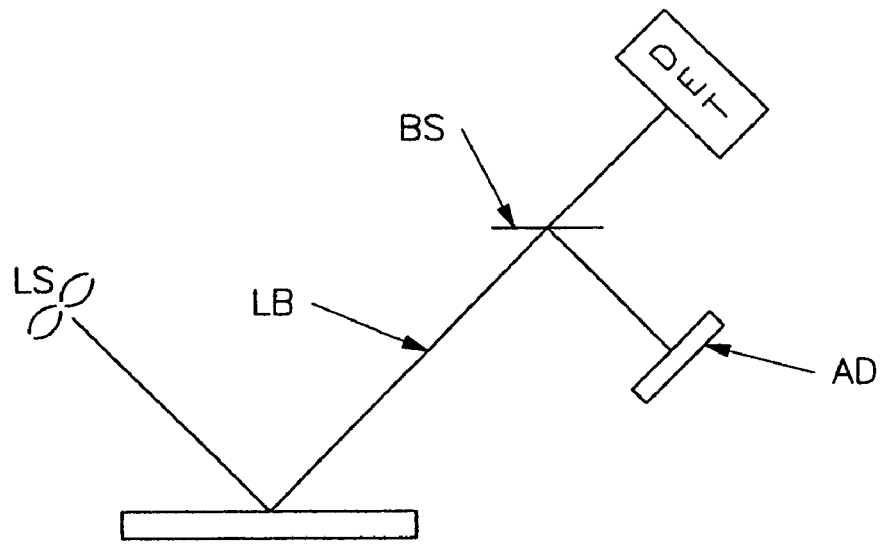
FIG. 7 shows a system which can be applied to provide a signal allowing "Z" distance adjustment.

FIGS. 5, 6 and 7 are included to demonstrate how signals indicating sample orientation with respect to "X" "Y" and "Z" orientations of the disclosed invention System (SYS) can be determined using Multi-Element Alignment Detectors (AD), said signals being provided to the disclosed invention Control Means (C). FIG. 5 demonstrates a Multi-Element (eg. Quad), Alignment Detector (AD). Note that electromagnetic radiation is shown reflecting from a Sample (S) and undergoing some dispersal such that each Quad Detector Element (Q1) (Q2), (Q3) and (Q4) receives some input. It should be appreciated that orientation of the Sample (S), (eg. as achieved via indicated rotation around the shown axes), determines the amount of electromagnetic radiation which enters the various Quad Detectors. Further, it should be appreciated that were the sample moved significantly downward in FIG. 5, all electromagnetic radiation would miss the shown Quad Alignment Detector (AD). FIG. 6 shows a configuration of an Alignment Detector which provides sensitivity to Sample Rotations, but not Vertical Height. FIG. 7 shows a configuration of an Alignment Detector which provides sensitivity to Sample Vertical Height. (Note that the Central Hole (CH) in the FIG. 5 Alignment Detector need not be present in the FIG. 7 embodiment as electromagnetic radiation need not pass therethrough.

FIG. 8 shows demonstrates a present invention ellipsometer system (SYS) situated on "X"-"Y" control means above a large sample (S). Indicated in block form are (LS) and (P), and (A) and (DET). A Cable is shown which can be used to provide power to, and transmit data from the ellipsometer system (SYS).

FIG. 9a is similar to FIG. 8, but has means added for flowing purging gas onto a sample at the point it is being investigated, during a period in which UV and IR wavelength Electromagnetism interacts therewith.

It is noted that a Large Sample can be a single piece such as a large slab of glass, or can consist of a multiplicity small samples place on a base. Further, while the surface is typically flat, it can comprise some third dimension projections.

In use the system selected from the group consisting of:
reflectometer;
rotating analyzer ellipsometer;
rotating polarizer ellipsometer;
rotating compensator ellipsometer;
modulation element ellipsometer;
Mueller Matrix measuring system;

can be thought of as "flying" over the sample.

Figure 9B:
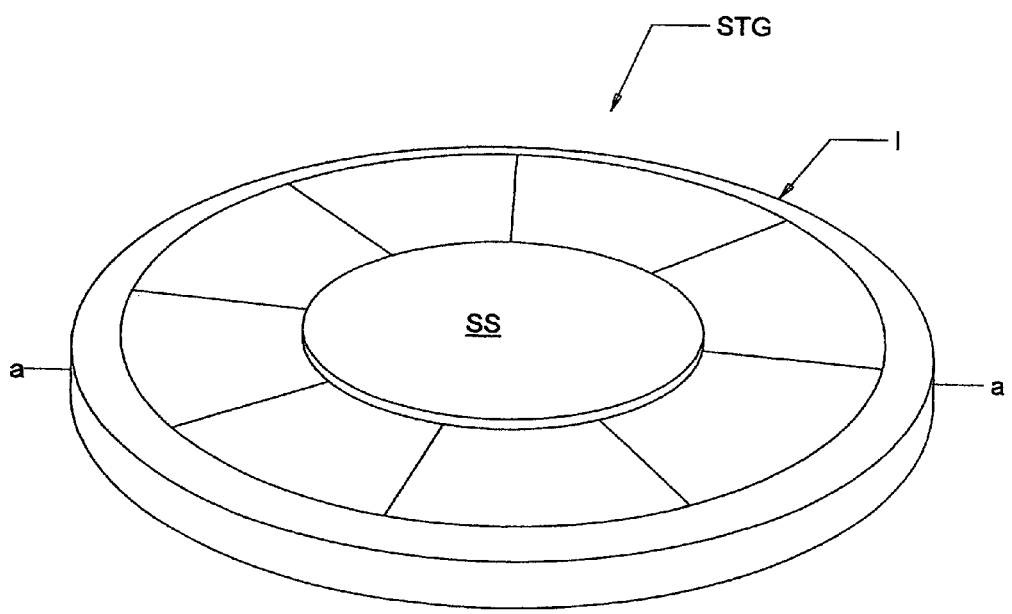
FIG. 9b shows a perspective view of a sample on a stage which includes an Interface (I) structure around its circumference.

FIG. 9b shows a perspective view of a Sample (SS) on a Stage (STG) which includes an Interface (I) structure around its circumference. Said Interface (I) can be a rigid or compliant structure and the surface thereof can be coated with a material such a teflon.

Figure 9C:
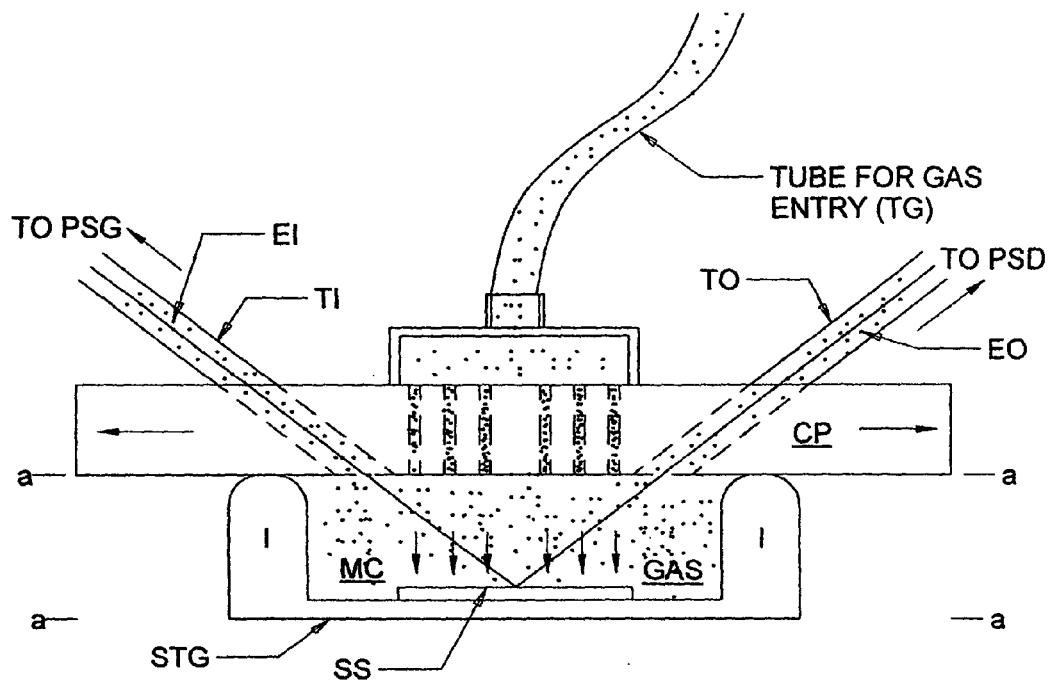
FIG. 9c shows a cross-sectional view taken a-a on FIG. 9b, showing a Stage (STG) and Sample (SS), wherein the Interface Means (I) affixed to the Stage (STG) is in slidable contact with a Common Placement Means (CP) to which it is indicated is mounted a (PSG) and (PSD) of electromagnetic radiation.
Figure 9D:
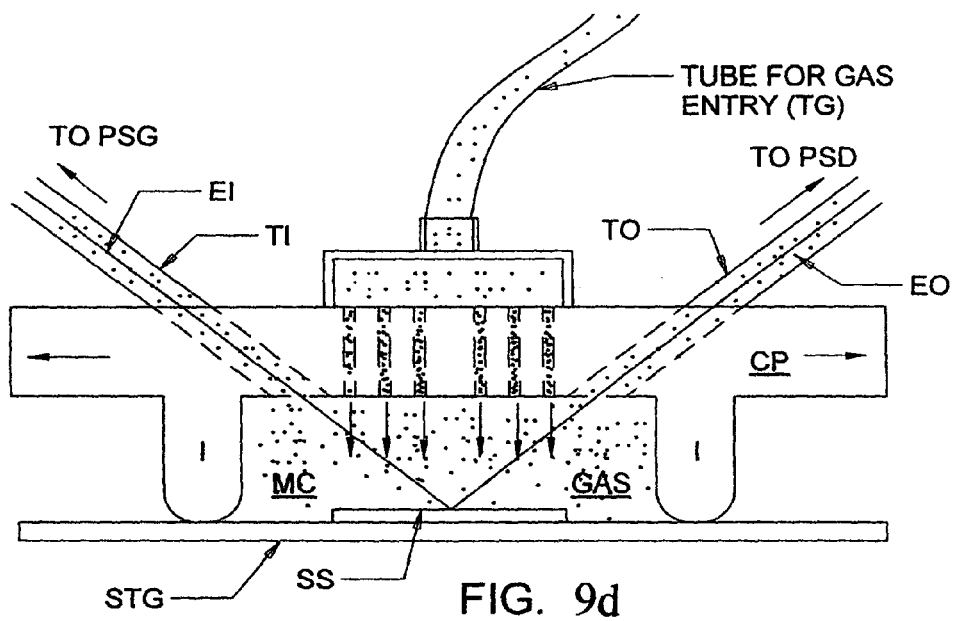
FIG. 9d shows a cross-sectional view as in FIG. 9c, but wherein the Interface Means (I) are affixed to the Common Placement Means (CP).
Figure 9E:
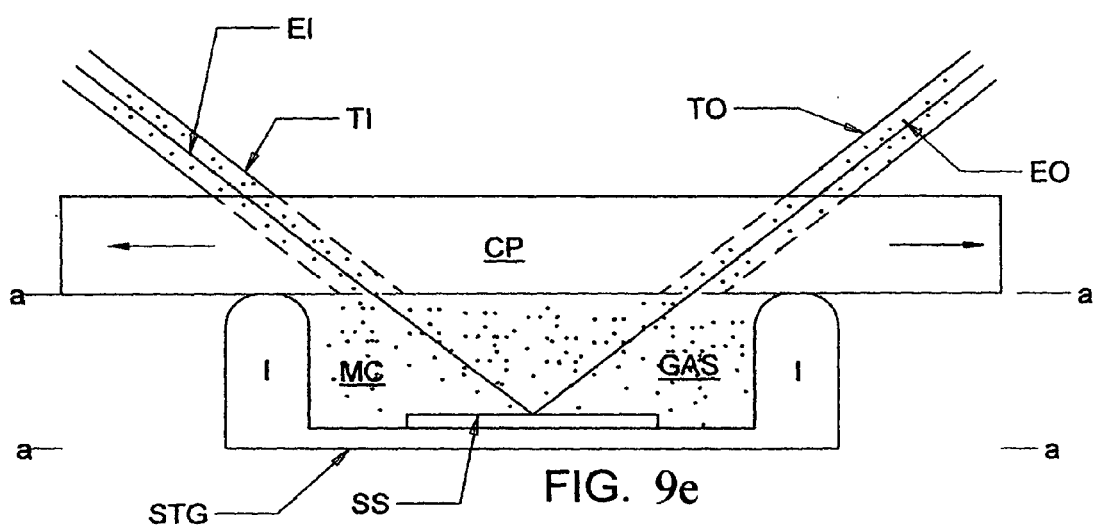
FIG. 9e shows a cross-sectional view taken a-a on FIG. 9b, showing a Stage (STG) and Sample (SS), wherein the Interface Means (I) affixed to said Stage (STG) is in slidable contact with a Common Placement Means (CP) to which it is indicated is mounted a (PSG) and (PSD) of electromagnetic radiation.

FIG. 9c shows a cross-sectional view taken a-a on FIG. 9b, showing a Stage (STG) and Sample (SS), wherein the Interface Means (I) affixed to the Stage (STG) is in slidable contact with a Common Placement Means (CP) to which it is indicated is mounted a (PSG) and (PSD) of electromagnetic radiation. Note that relative lateral motion of the Common Placement Means (CP) and Interface (I) is possible via sliding of the Common Placement Means (CP) over the Interface (I). FIG. 9d shows a cross-sectional view as in FIG. 9c, but wherein the Interface Means (I) are affixed to the Common Placement Means (CP) and a sliding lateral motion is enabled between the Interface Means (I) and the Stage STG). Note that FIGS. 9c and 9d provide separate GAS entry means via a Tube (TG) for Entering Gas. FIG. 9e shows a cross-sectional view taken a-a on FIG. 9b, showing a Stage (STG) and Sample (SS), wherein the Interface Means (I) affixed to said Stage (STG) is in slidable contact with a Common Placement Means (CP) to which it is indicated is mounted a (PSG) and (PSD) of electromagnetic radiation. Note that the GAS is entered and exits through Tubes (TI) (TO) via which electromagnetic radiation (EI) (EO) is entered and exits. It is to be appreciated that the embodiments shown in FIGS. 9c and 9d can also provide GAS via the Tubes (TI) and (TO).

Figure 9H:
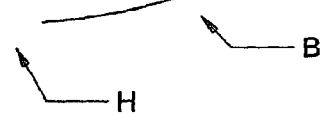
FIGS. 9h and 9i show two embodiments of a Bellows (B). Fig. a shows a small Hole (H) is present at a location whereat electromagnetic radiation would exit and impinge on a Sample (SS)
Figure 9I:
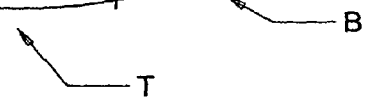
Figure 9F:
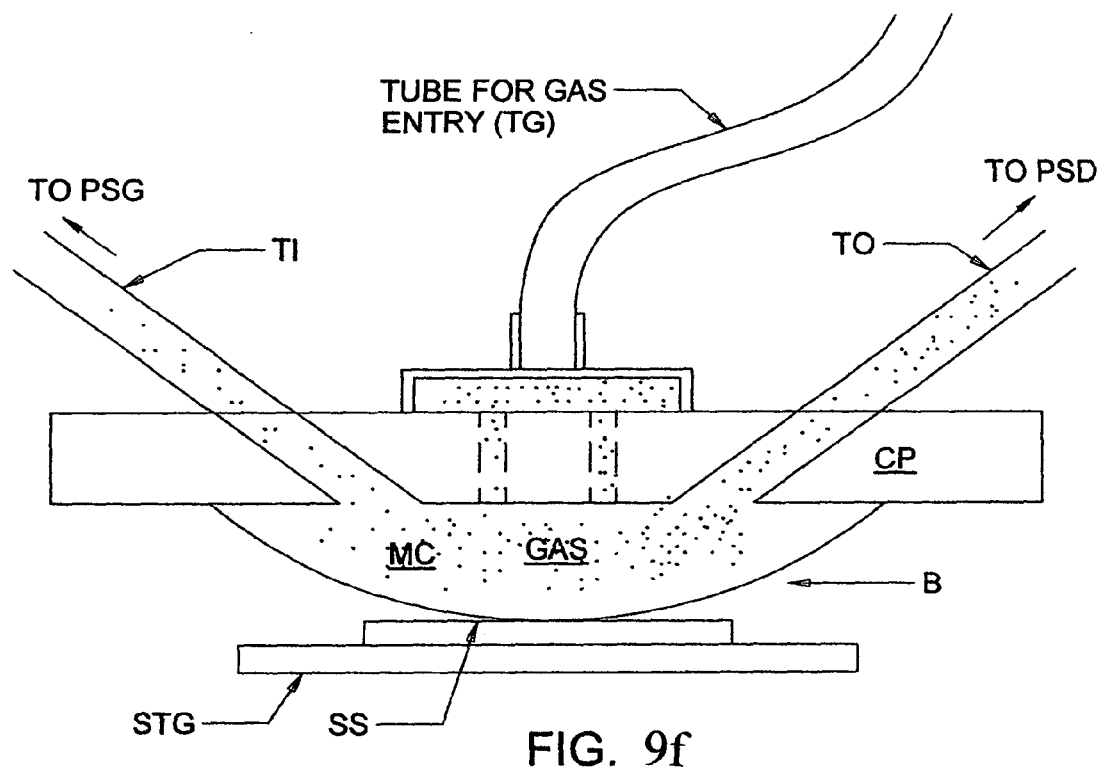
FIGS. 9f and 9g show a modified embodiment wherein a Bellows (B) is affixed to the Common Placement Means which in use is filled with gas such that it is placed directly adjacent to a surface of a Sample (SS).
Figure 9G:
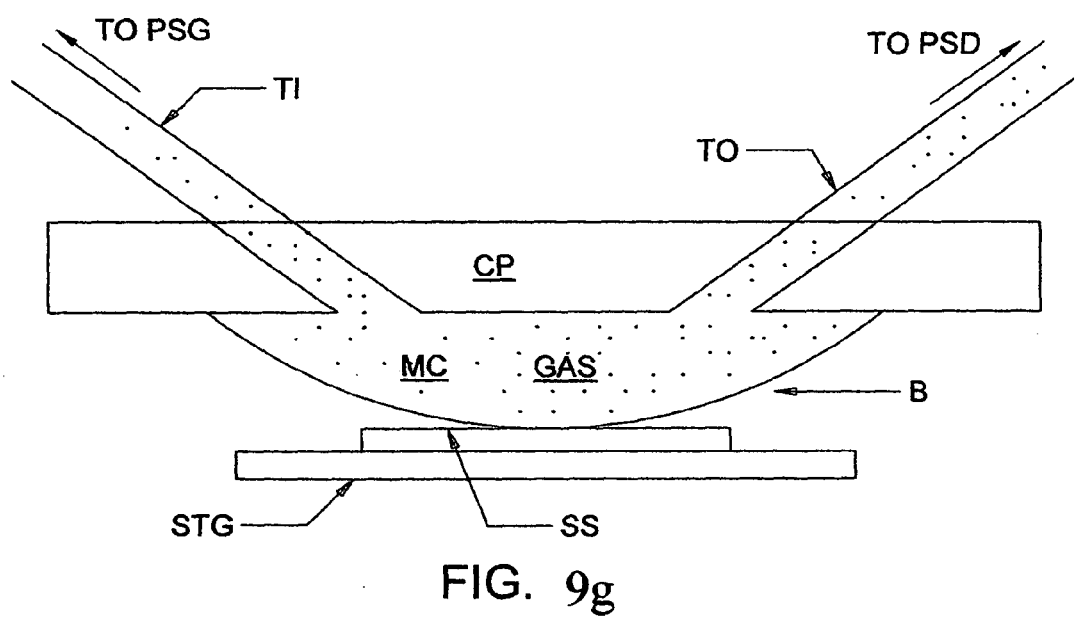

FIGS. 9f and 9g show a modified embodiment wherein a Bellows (B) is affixed to the Common Placement Means which in use is filled with gas such that it is placed directly adjacent to a surface of a Sample (SS). While the Common Placement Means (CP) can be moved to position the lower aspect of the Bellows (B) into contact with a Sample (SS), this embodiment enables contact via inflating the Bellows (B).

FIGS. 9h and 9i show two embodiments of a Bellows (B). FIG. 9h shows a small Hole (H) is present at a location whereat electromagnetic radiation would exit and impinge on a Sample (SS), and FIG. 9i shows that a region (T) which is transparent to applicable wavelengths is present. The remainder of the Bellows can be opaque to wavelengths in the UV, VUV, IR and NIR.

In general it should be appreciated that in FIGS. 9c, 9d, 9e, 9f, 9g, 9j and 9k that a "Mini-Chamber" (MC) is formed in which GAS is sequestered. In FIGS. 9c and 9e this is effected by vertically moving the Common Placement Means (CP) so that the Interface Means (I) is brought into contact therewith. In FIG. 9d said vertical motion provides contact between the Interface Means (I) and the Stage (STG). It is noted that the Common Placement Means (CP) can be of single or multiple element construction, and that contact can mean "substantial contact" where the Common Placement Means (CP) and the Interface Means (I) are nearly in contact with one another.

Figure 9J:
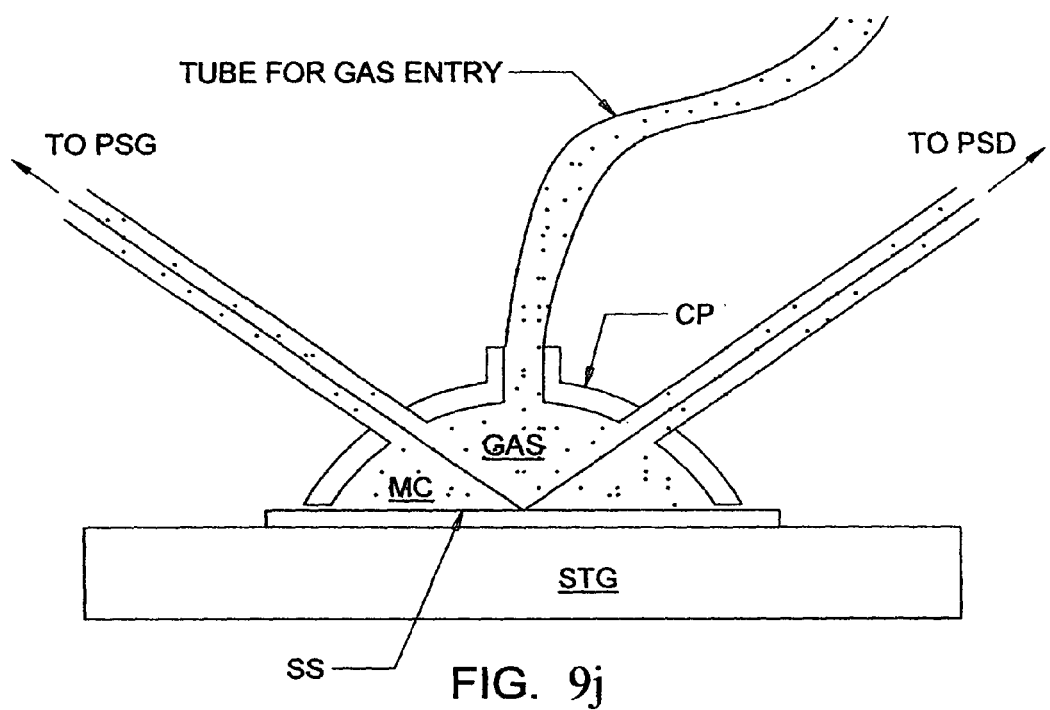
FIGS. 9j and 9k show embodiments of the present invention wherein a portion of a sample (SS) is sequestered in a mini-chamber.
Figure 9K:
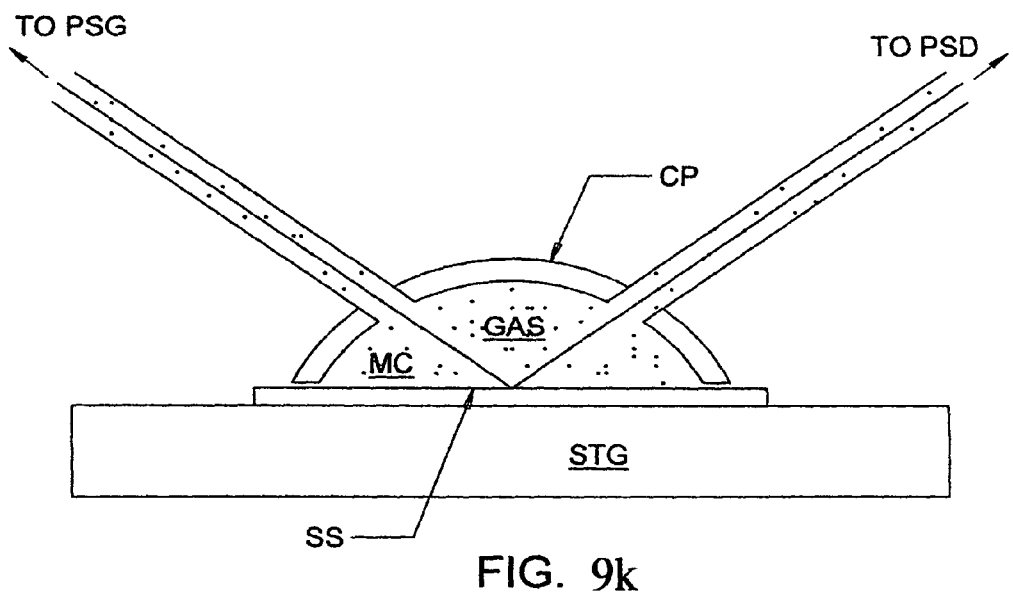

FIGS. 9j and 9k show embodiments of the present invention wherein a portion of a sample (SS) is sequestered in a 20. Mini-Chamber (MC) which is formed by causing said Common Placement Means (CP) to actually contact a portion of a sample (SS). Note that the Common Placement Means (CP) need not have a planar surface facing the Sample (SS). The Common Placement Means (CP) can be constructed from one or more elements, and the Polarization State Generator (PSG) need not be affixed to the same element as is the Polarization State Detector (PSD) as long as said (PSG) and (PSD) can be caused to move together in a coordinated manner. The same is applicable to the embodiments shown in FIGS. 9c, 9d and 9e.

It is to be understood that while the foregoing presentation has focused on the use of gas to tangibly and concretely purge a "mini-chamber", it is possible to reverse to approach and apply an evacuation pump to tangibly and concretely decrease atmospheric content in a "mini-chamber", which can be, but is not necessarily followed by entering a purge gas thereinto.

It is also noted that while not limiting, the Stage (STG) for securing a Sample System can conveniently include a vacuum chuck which allows easily securing and releasing the sample by providing a suction, or not. In addition, the Stage (STG) for securing a Sample System can also contain a heating and/or cooling means for controlling the temperature of a sample.

In the forgoing, and in the Claims, recitation of "a beam having UV, VUV, IR and NIR wavelengths of electromagnetic radiation" is not to be interpreted to exclude the presence of Visible wavelengths. However, said Visible wavelengths are not specifically mentioned as they are not as susceptible to attenuation by $O_2$ and Water Vapor.

It is also noted that the Interface Means (I) can be rigid or non-rigid. Further, the Interface Means (I) can be in actual contact with, or in substantial contact with, (eg. a millimeter or more removed from actual contact with), a sample or stage and be considered slidably in contact therewith the criteria being that it is not so far removed so as to let gas flow therefrom unimpeded.

Figure 16:
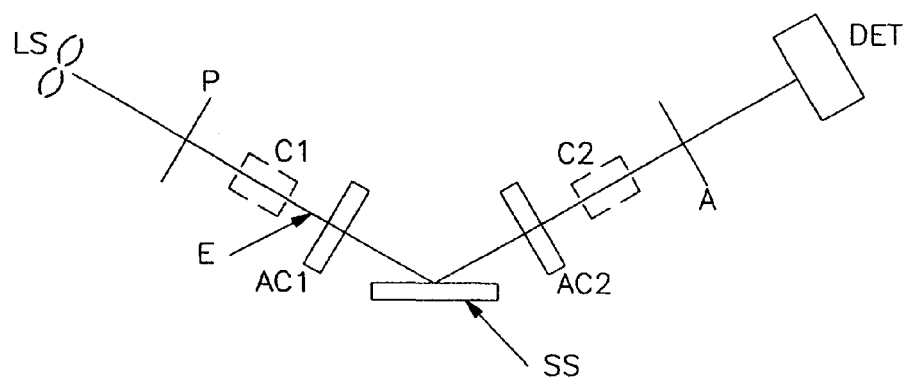
FIG. 16 shows a more detailed presentation of an ellipsometer system to which the Present Invention is applied.
Figure 17A:
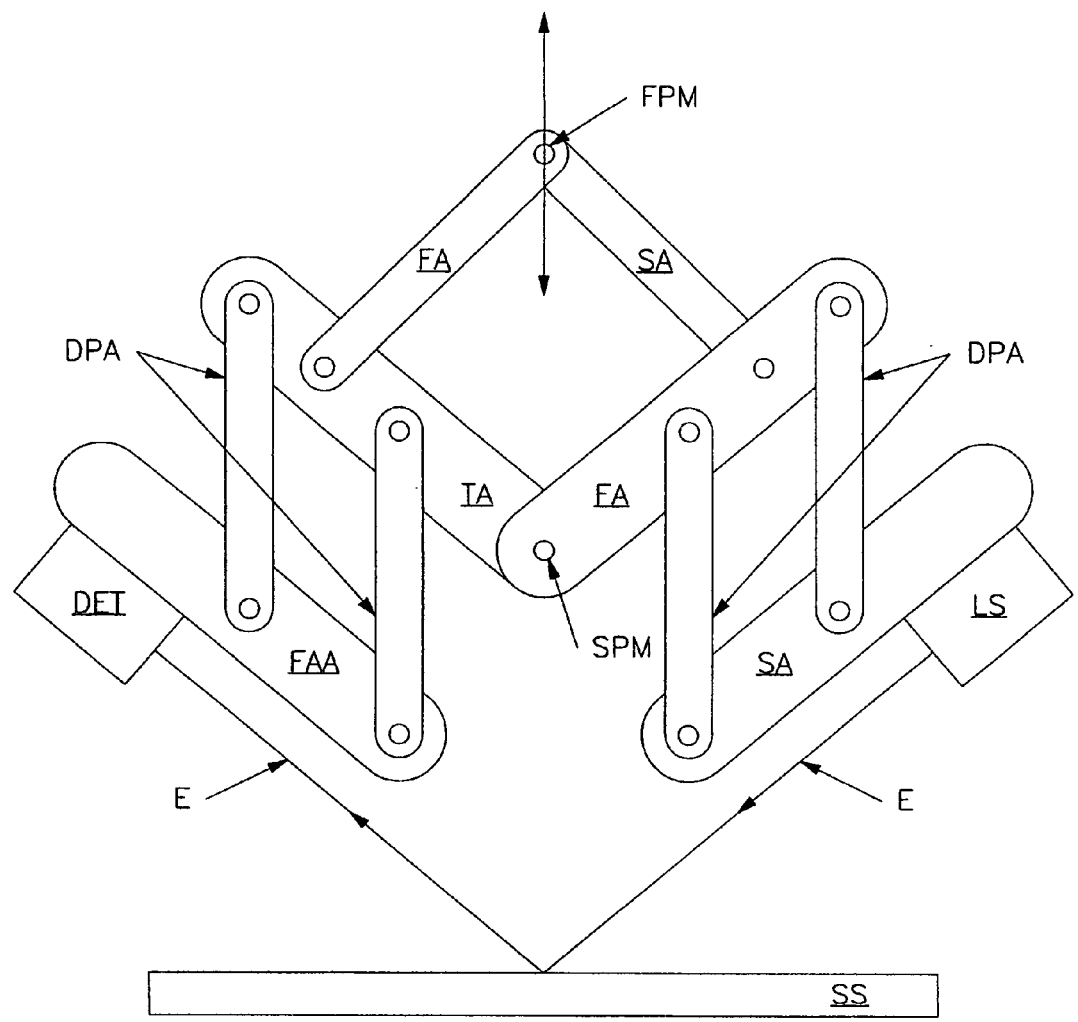
FIG. 17a shows an approach to mounting Ellipsometer Polarization State Generator and Polarization State Analyzer Systems which allow easily changing the Angle-Of-Incidence of a Beam of Electromagnetic radiation caused to impinge on a Sample, as well as easily change the vertical height of thereof above the Sample.
Figure 17B:
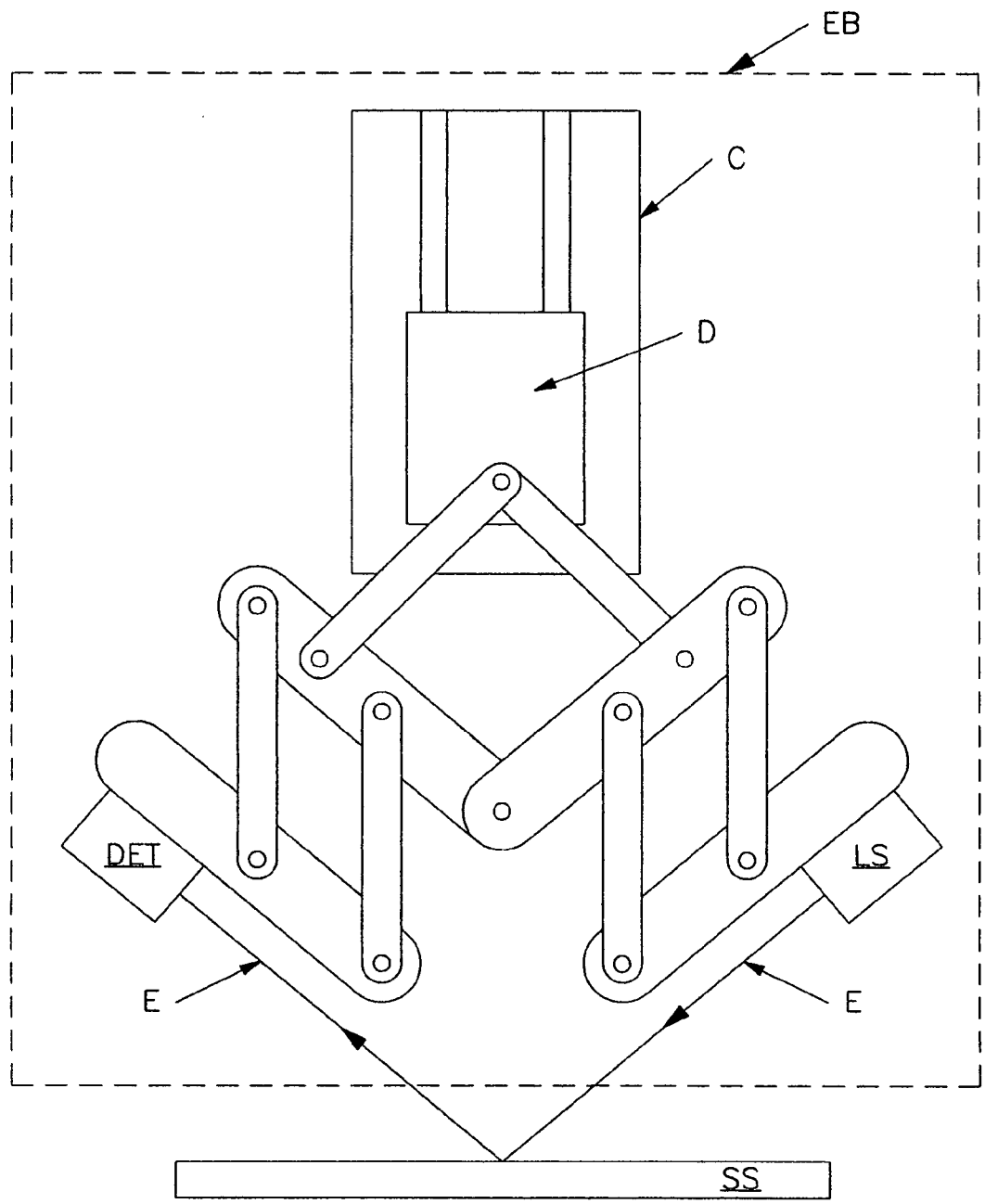
FIG. 17b shows the system of FIG. 17a indicated as present in a modified version of FIG. 2

Continuing, FIGS. 10-16 describe Angle-of-Incidence changing systems which can be added to the system of FIG. 2, and FIGS. 17a and 17b demonstrate an alternative system which can replace the FIG. 2 embodiment.

Figure 10:
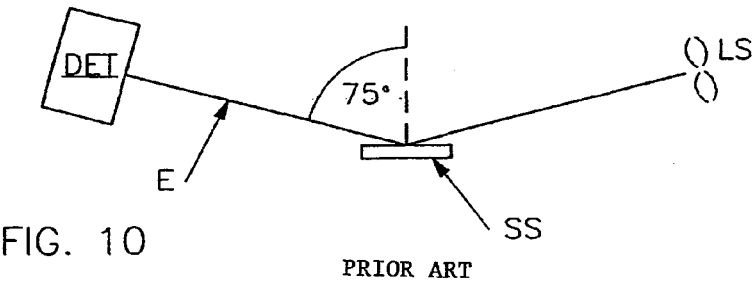
FIG. 10 shows a Front View of a Conventional Ellipsometer, Polarimeter or Reflectometer System with an Electromagnetic Beam shown approaching and reflecting from a sample system at an (AOI) of, for instance, 75 degrees.
Figure 11:
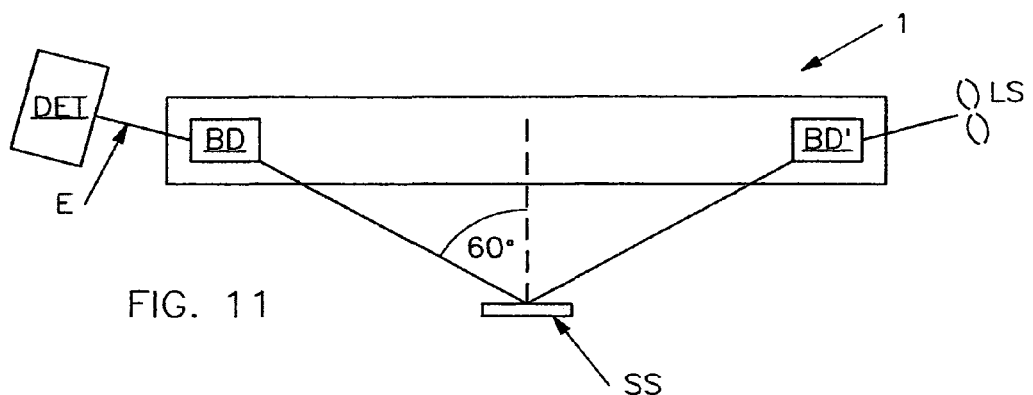
FIG. 11 shows that the (AOI) is changed to, for instance, 60 degrees when a Present Invention System (1) is placed in the pathway of the Electromagnetic Beam.
Figure 12A:
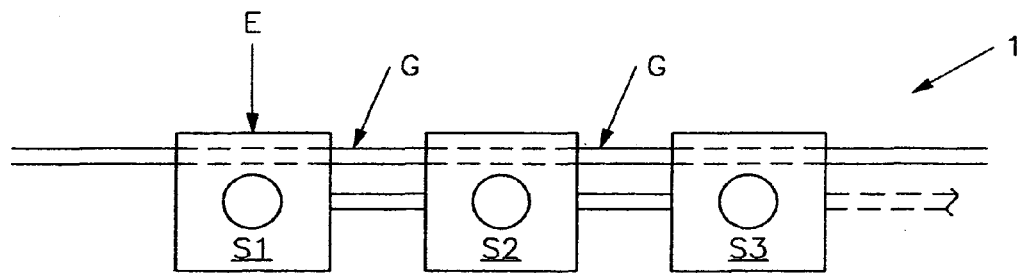
FIG. 12a shows a Side View of Present Invention System(s) (S1) (S2) (S3) mounted on a Guide (G) upon which they can be slid right and left. Present Invention System (S1) is shown slid into position to intercept Electromagnetic Beam (E).
Figure 12B:
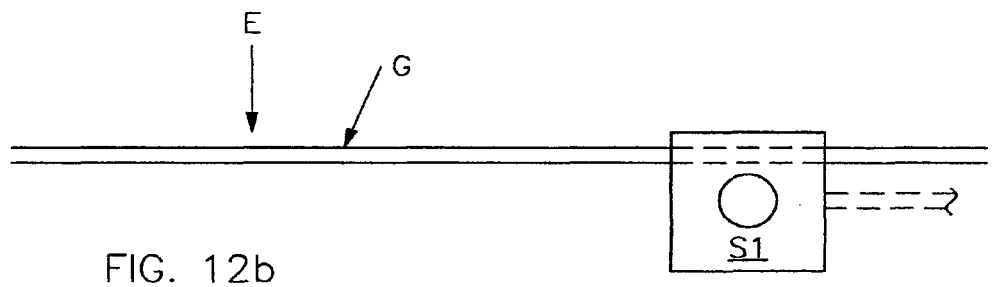
FIG. 12b shows a Side View of the system shown in FIG. 3a with Present Invention System(s) (S1) (S2) (S3) slid to the right therein such that none thereof intercepts Electromagnetic Beam (E).

FIG. 10 shows a Front View of a Material System Investigating System, (eg. Ellipsometer, Polarimeter, Reflectometer or Spectrophotometer System), with an Electromagnetic Beam shown approaching and reflecting from a Sample System (SS) at an (AOI) of, for instance, 75 degrees with respect to normal. FIG. 11 shows that the (AOI) is changed to, for instance, 60 degrees with respect to normal when a disclosed invention electromagnetic beam intercepting angle-of-incidence changing system (1) is placed in the pathway of the Electromagnetic Beam. FIG. 12a shows a Side View of a disclosed invention electromagnetic beam intercepting angle-of-incidence changing system mounted on a Guide (G) upon which they can be slid right and left. The location of a Materials System Investigating System with respect to the disclosed invention electromagnetic beam (E) intercepting angle-of-incidence changing system is indicated by (E), which is the same (E) indicated in FIGS. 10 and 11. Referral to FIGS. 12a and 12b shows that a sliding motion to the left will place a disclosed invention electromagnetic beam intercepting angle-of-incidence changing system (S1) (S2) (S3) in the pathway of an Ellipsometer System Electromagnetic Beam (E), (see FIG. 12a), and sliding disclosed invention electromagnetic beam intercepting angle-of-incidence changing system to the right moves them out of the Electromagnetic Beam, (see FIG. 12b). (Note right and left in FIGS. 12a and 12b correspond to a perpendicular to the plane of the surface of the paper in FIGS. 10 and 2.

FIG. 13 shows a Multiangle Prism (MAP) in a disclosed invention Electromagnetic Beam (E) intercepting Angle-of-Incidence changing system (1), on the left side thereof, (as indicated (BD) in FIG. 12). Note that the orientation of the (MAP) increases the (AOI) in FIG. 13, whereas in FIGS. 12, (and 14a), the (MAP) is oriented to decrease the (AOI). FIG. 14a shows how a Multiangle Prism (MAP) changes the pathway of an Electromagnetic Beam by Total Internal Reflection therewithin. The shapes and materials which characterize the prisms can be designed and selected to cause the (desired (AOI) change, as well as effect phase shifts entered by total internal reflections to be stable, or at least have small sensitivity to changes in (AOI). Polymer for Far IR, Silicon or Germanium for IR, and Quartz for UV, VIS-NIR or CaF for VUV, for instance, can be utilized. And note that a two or more Multiangle Prisms can be present on at least one side of the sample system, to provide an (AOI) not possible where only one is present. FIG. 14b shows a plurality of mirrors (M) (M') can also form disclosed invention electromagnetic beam intercepting angle-of-incidence changing system. FIG. 13 also shows Optional Lenses (OL) can be positioned to focus a beam of electromagnetic radiation onto a spot on a sample system. Said Optional Lenses (OL) can be independently mounted, or affixed to the Multiangle Prisms (MAP). Note, it is possible to have two "Present Invention Systems" which provide the same AOI, one having Optional Lenses for focusing present, and the other not.

Figure 14C:
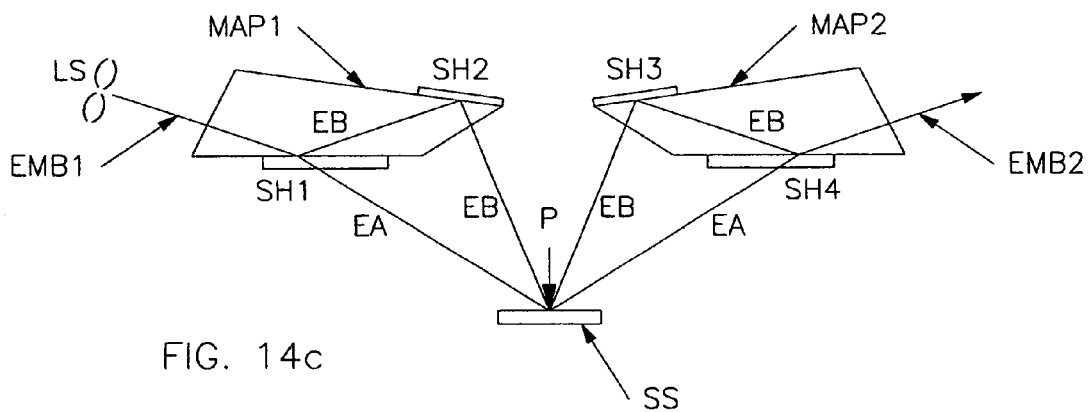
FIG. 14c shows additional configurations of Multiple Angle Prisms (MAP1) and (MAP2) which have Shutters (SH1) & (SH2), and (SH3) & (SH4) respectively present thereupon.
Figure 14D:
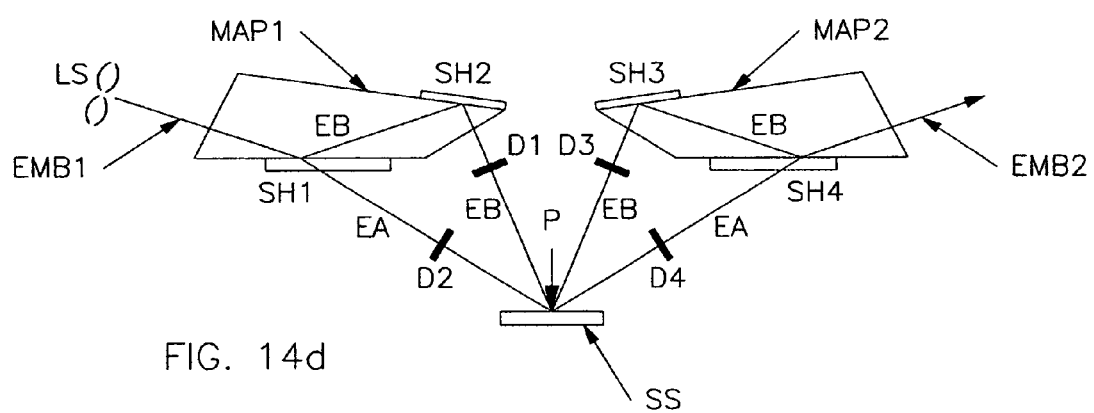
FIG. 14d shows FIG. 14c with door shutters (D1), (D2), (D3) and (D4) present therein.

FIGS. 14c and 14d show additional configurations of Multiple Angle Prisms (MAP1) and (MAP2) which have Shutters (SH1) & (SH2), and (SH3) & (SH4) respectively present thereupon. Said Shutters (SH1) & (SH2), and (SH3) & (SH4) can be, for instance, voltage controlled liquid crystals or electromagnetic-optics means for effectively changing the refractive index of the top and bottom surfaces of a multiangle prism, for the purpose of controlling the internal reflection/transmission properties. FIG. 14c shows Input Electromagnetic Beam (EMB1) entering Multi-Angle Prism (MAP1) and interacting with the interface between said Multi-Angle Prism (MAP1) and said Shutter (SH1). If said interface is substantially transmissive then Beam (EA) proceeds to the Sample System, and reflects therefrom at point (P). Said Beam (EA) then proceeds through Multi-Angle Prism (MAP2) and exits therefrom as Output Electromagnetic Beam (EMB2). If, however, the interface between said Multi-Angle Prism (MAP1) and said Shutter (SH1) is substantially reflective, it should be appreciated that Input Electromagnetic Beam (EMB1) will reflect thereat and become beam (EB). It is to be assumed that the interface between said Multi-Angle Prism (MAP1) and said Shutter (SH1) is also substantially reflective, so that beam (EB continues to reflect from Sample System, and reflects therefrom at point (P), and continue through Multi-Angle Prism (MAP2), wherein it interacts with reflective interfaces between said Multi-Angle Prism (MAP1) and said Shutters (SH3) & (SH4) to emerge as Output Electromagnetic Beam (EMB2).

FIG. 14d shows FIG. 14c with additional Physical Door-Shutter means (D1), (D2), (D3) and (D4) in place to further enhance the Transmission/Reflection effect described with respect to FIG. 14c. For instance, when the interface between Multi-Angle Prism (MAP1) and said Shutter (SH1) is substantially transmissive, Physical Door-Shutter (D2) will be open and Physical Door-Shutter (D1) will be closed. The operation of Said Physical Door-Shutter means (D1), (D2), (D3) and (D4) must, of course, be coordinated with operation of Shutters (SH1) & (SH2), and (SH3) & (SH4), but when present serve to essentially completely overcome the effect of any imperfect operation of Shutters (SH1) & (SH2), and (SH3) & (SH4).

Figure 14E:
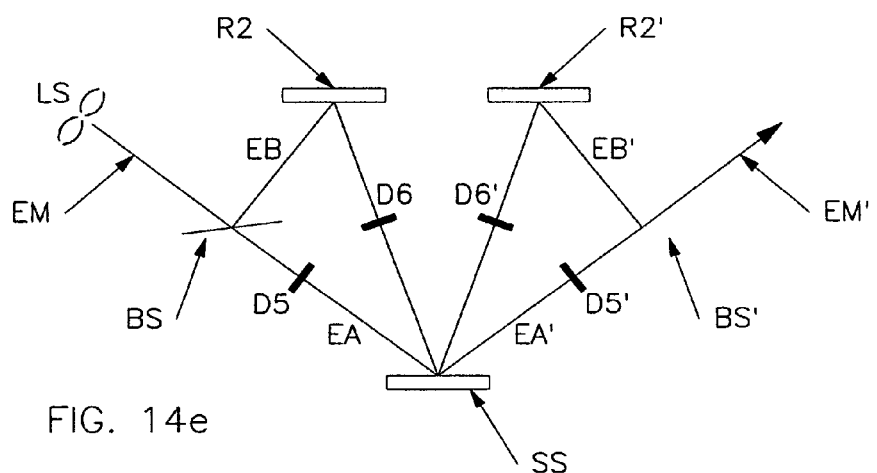
FIG. 14e shows a system for providing multiple angles-of-incidence utilizing Beam Splitter, Reflective means and shutter doors.
Figure 14F:
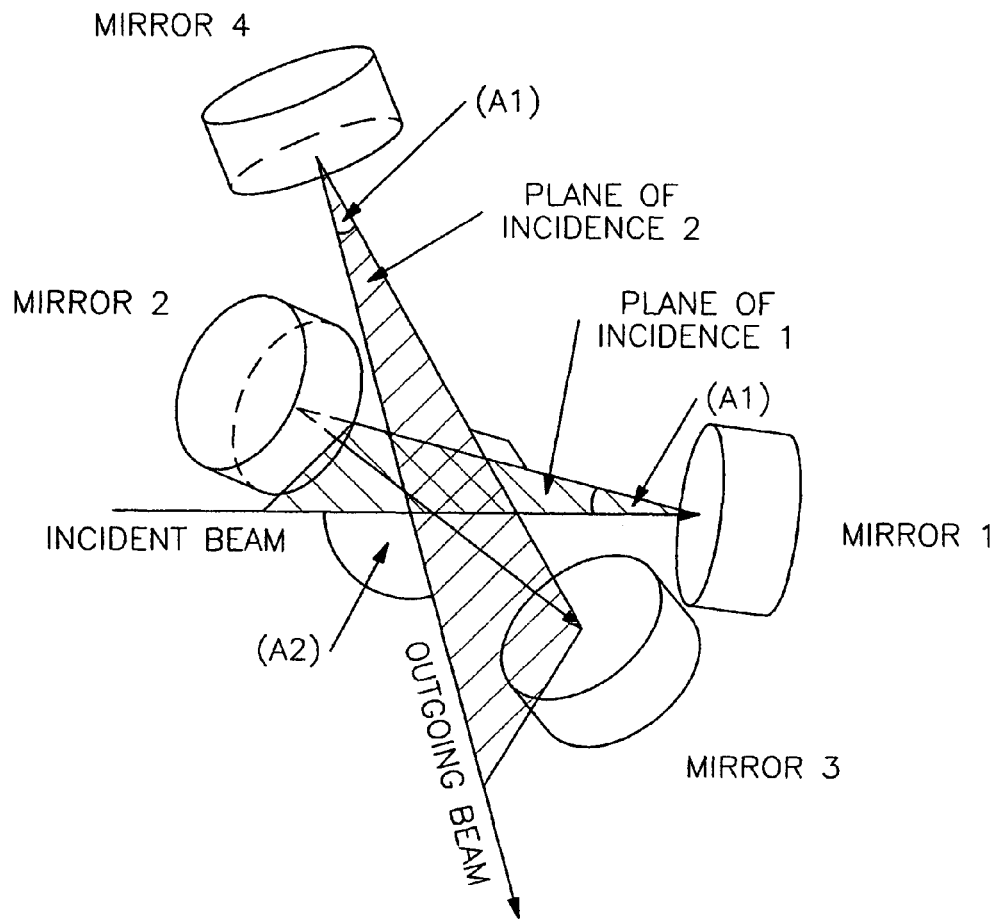
FIG. 14f shows a particularly relevant way to use reflective means to alter the trajectory of a Beam of electromagnetic Radiation, without significantly changing the phase angle between orthogonal components thereof.

FIG. 14e shows an alternative system for effecting different angles of incidence. Note that a Beam Splitter (BS) receives a Beam of Electromagnetic Radiation (EM) and continuously reflects approximately half (EB) and transmits (EA) the remainder. The reflected portion (EB') reflects from a Second Reflection means (R2). Both the reflected (EB') and Transmitted (EA) Electromagnetic Beams arrive at the same point on Sample System (SS), but at different angles-of-incidence. Note, importantly, that Door Shutters (D5) and (D6) are present, and are operated to block one or the other of (EA) and (EB') when desired. After the Sample System (SS), whether it is electromagnetic beam (EA) or (EB') which is allowed to proceed, note that it makes its way to the Detector (DET) by a pathway which is a mirror image to that which brought it to the Sample System (SS) from the Electromagnetic Beam Source. Note that typically four shutter doors (D5) (D6) (D5') (D6') are be present, two on each side of the sample system (SS), said shutter doors being positioned in the loci of the electromagnetic beams which transmit through (EA) and reflect from (EB') the beam splitter (BS) on the incident side of the means for supporting a sample system (SS).

It is important to mention U.S. Pat. No. 5,969,818 to Johs et al. which is incorporated hereinto by reference. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair. The Reflector (R2) in FIG. 14e, (and a similar Reflector in an output side) can comprise Patent 818 Beam Folding Optics. FIG. 5 from said 818 Patent is reproduced herein as FIG. 14f. Note that Beam (EB) in FIG. 14e is shown as is Beam ((EB'), and that Mirrors 1 and 2 form a First Pair, and Mirrors 3 and 4 a Second Pair. Note how the Planes of incidence 1 and 2 are orthogonally related to one another. It is not a focus of Patentability herein to specify any particular FIG. 14e Second Reflective Means (R2) system. The FIG. 14f system is, however, identified as a particularly relevant way to use reflective means to alter the trajectory of a Beam of Electromagnetic Radiation, without significantly changing the phase angle between orthogonal components thereof. Such an effect is similar to that provided by Total Internally Reflective Multi-Angle Prisms, as shown in FIGS. 13, 14a, 14c and 14d herein.

The disclosed invention system also typically includes means for adjusting, for instance, tilt, translation and rotation orientations of the multi-angle prisms and/or the Optional Lenses (OL) within the containing structure. Such presence facilitates easy system set-up optimization. FIG. 15 demonstrates mounting Bases (B1), (B2) and (B3) mounted with respect to one another so that mounting Base (2) can move right and left on mounting Base (1), and so that mounting Base (3) can rotate on mounting Base (2). A Multiangle Prism (MAP) is shown mounted to mounting Base (3). Mounting Base (1) can of course be mounted in a Present Invention Electromagnetic Beam (E) intercepting Angle-of-Incidence (AOI) changing system (1), as shown in FIG. 12, in the position of (BD) or (BD') in a manner to allow it Rotational or any Linear Degrees of Motion Freedom. In particular motion into and out of the place of the paper is also possible at the (B1), (B2) and/or (B3) level, as required. Note that an Optical Lens (OL) is also shown rotatably and translatably mounted via mounting Base (B4) to mounting Base (1). This is an optional feature, and it is noted that the Optical Lens (OL) can be absent, or separately mounted. FIG. 15 is to be considered only demonstrative, and functional mountings can include any required translation, tilt and rotation adjustment capability shown, and not directly shown or visible in the view presented.

It is also to be appreciated that while an Electromagnetic Beam (E) which interacts with a Sample System (SS) will often be polarized, where the disclosed invention system (1) is used with a Reflectometer System, this need not be the case. Reflectometers which produce unpolarized electromagnetic radiation and cause impingement at oblique (AOI's), (instead or in addition thereto ellipsometer produced beams), can have the disclosed invention applied thereto as well.

FIG. 16 provides a general elemental configuration of an ellipsometer system (10) which can be applied to investigate a sample system (SS). Shown are, sequentially:

a. a Source of a beam electromagnetic radiation (LS);
b. a Polarizer element (P);
c. optionally a compensator element (C1);
d. (additional element(s)) (AC1);
e. a sample system (SS);
f. (additional element(s)) (AC2);
g. optionally a compensator element (C2);
h. an Analyzer element (A); and
i. a Detector System (DET).

It is noted that the elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the disclosed invention Disclosure, input and output electromagnetic beam intercepting angle-of-incidence changing system elements. (Note the presence of indication of an Electromagnetic Beam (E) in FIG. 16, which for orientation it is noted corresponds to the location shown in FIGS. 12, 12*a* and 12*b*).

Where, as is generally the case, input (AC1) and output (AC2) additional elements, (eg. multiangle prisms or functional equivalents as represented by (BD) and (BD') in FIG. 12), have bi-refringent characteristics, it must be appreciated that said characteristics must be accounted for in a mathematical model of the ellipsometer and sample system.

It is to be appreciated that single systems shown FIGS. 14*c*, 14*d*, 14*e* can be fixed in place and various shutters and door shutters operated to effect beam directing. However, multiple embodiments shown in said FIGS. 14*c*, 14*d* and 14*e* can be mounted to a slidable means to enable effecting any of a plurality of angles-of-incidence. Once in place however, two angles-of-incidence can be effected by a FIG. 14*c*, 14*d* or 14*e* system without physically moving it into an out of a beam of electromagnetic radiation.

It is beneficial at this point to refer to the paper by Johs, titled "Regression Calibration Method for Rotating Element Ellipsometers", which was referenced in the Background Section of this Disclosure. Said paper describes a mathematical regression based approach to calibrating rotating element ellipsometer systems. Said calibration procedure provides that data, (eg. ellipsometric ALPHA and ellipsometric BETA values), be obtained as a function of an ellipsometer system Polarizer Azimuth, as said Polarizer Azimuth is stepped through a range of angles, (eg. sixty (60) degrees to one-hundred-sixty (160) degrees). A mathematical model of the ellipsometer system and a sample system under investigation is provided, and a mathematical square error reducing technique is applied to evaluate parameters in said mathematical model. Successful calibration leads to experimental data and calculated data curves being essentially coincident.

Further insight to the benefit of applying 630 Patent-type regression calibration, and 777 Patent window-like effect corrections to ellipsometer and the like systems which include the disclosed invention multiple-AOI providing system, having then been illuminated herein, can be found in said 630 and 777 Patents which are incorporated by reference in this Specification. Said 777 Patent demonstrates that a methodology for correcting for affects of acquiring ellipsometric data through standard vacuum chamber windows, which can be applied to correcting affects of disclosed invention (AOI) changing systems, has been developed and tested. The key insight enabling said accomplishment is that bi-refringence can be split into "out-of-plane" and "in-plane" components, where the "plane" referred to is the plane of incidence of an electromagnetic beam of radiation with respect to a sample system. Splitting the electromagnetic beam into said orthogonal components allows derivation of second order corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a sample system DELTA. A separate step, utilizing a sample system for which retardation can be modeled by a parameterized equation, allows evaluation of the parameters in parametric equations for the "in-plane" components of windows separately. Work reported in the literature by other researchers provided equations which corrected only first order effects, and said equations have proven insufficient to correct for large, (eg. six (6) degrees), of retardation which is typical in standard vacuum chamber windows and which can occur in disclosed invention (AOI) changing systems. It is noted that each total internal reflection in a multiangle prism can impart up to about 45 degrees retardance, depending on the internal reflection angle. Four such bounces can then impart on the order of 160 degrees total phase retardance between the electromagnetic beam orthogonal components.

Continuing to use vacuum chamber windows as example, it is noted that said prior work orthogonal components were derived with respect to window fast axes, which is offset from the sample system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a sample system DELTA parameter unless a global regression fit using a parameterizable sample system is performed at calibration time. Said methodology comprising two steps as disclosed herein, fully and unambiguously determines correction terms in-situ.

After parameters in parameterized equations for retardance are evaluated by the method of the disclosed invention, ellipsometric data can be taken through disclosed invention (AOI) changing systems and said data can be quickly and accurately analyzed by applying the correction factors in a mathematical model for a sample system, (in the case where a Rotating Analyzer ellipsometer system was used to acquire data), or the (AOI) changing system effects can be simply quantitatively subtracted away to yield "true" ellipsometric PSI and DELTA values, (in the case where a Rotating Compensator ellipsometer system was used to acquire data). It is noted that the Patent to Johs et al. U.S. Pat. No. 6,034,777, provides demonstrative data obtained by practice of the described correction methodology as applied to other systems. Said data is incorporated by reference herein and should be considered as demonstrative of results obtained when it is applied to systems including disclosed invention (AOI) changing systems.

It is noted that shutters (SH1) (SH2) (SH3) (SH4) and shutter doors (D1) (D2) (D3) (D4) (D5) (D6) (D5') (D6') can be of any functional type, such as mechanical or voltage driven liquid crystal devices.

FIGS. 17*a* and 17*b* show a mechanical system for mounting a Reflectometer or Spectrophotometer Source and Detector, or Ellipsometer or Polarimeter Polarization State Generator, (eg. Source, Polarizer and optionally compensator), and Polarization State Analyzer, (eg. optional Compensator, Analyzer and Detector), Systems. Said approach to mounting allows easily changing the Angle-Of-Incidence of a Beam of Electromagnetic radiation caused to impinge on a Sample. Said system for setting the angle of incidence of a beam (E) of electromagnetic radiation comprises, as viewed in elevation, First (FA) and Second (SA) arms pivotally interconnected to one another at an upper aspect thereof by a First Pivot Means (FPM), said first (FA) and second (SA) arms projecting downward and to the left and right of said First Pivot Means (FPM); distal ends of said First (FA) and Second (SA) arms being pivotally affixed to Third (TA) and Forth (FA) arms, said Third (TA) and Forth (FA) arms being pivotally interconnected to one another by Second Pivot Means (SPM) at a lower aspect thereof, said Third (TA) and Forth (FA) arms being projected upward and to the left and right of said Second Pivot Means (SPM) at said lower aspect thereof; there being at least two pivotally affixed substantially Downward Projecting Arms (DPA) to each of said Third (TA) and Forth (FA) arms, distal ends of which are pivotally affixed to Fifth (FAA) and sixth (SA) arms which are not interconnected to one another, but project upward to the left and right, respectively. There are affixed to one of said Fifth (FAA) and Sixth (SA) arms a Source (LS) of a beam of electromagnetic radiation, and to the other of said Sixth (SA) and Fifth (FAA) arms a Detector (DET) of said Beam (E) of electromagnetic radiation. There is further a Sample (SS) located such that a Beam (E) of electromagnetic radiation produced by said Source (LS) of a beam of electromagnetic radiation reflects from an upper surface of said Sample (SS) and enters said detector of said beam of electromagnetic radiation, such that in use when the First Pivot Means (FPM) at which said First (FA) and Second (SA) arms are interconnected is caused to be vertically raised or lowered, the angle of incidence at which the Beam (E) of electric radiation approaches said sample surface is changed, but the location at which it interacts with said Sample (SS) surface remains substantially unchanged.

It is noted that designators (E), (EM), (EMB1), (EMB2) in the various Figures all identify a Beam of Electromagnetic Radiation from a Source (LS) thereof.

It is also noted that FIG. 17b shows the system of FIG. 17a in a Black Box (EB) much like FIG. 2 showed an Ellipsometer of an alternative design. Likewise, FIGS. 10, 11, 13 and 14a-14e show Sources (LS) and Detectors (DET) which can be considered to be those in FIG. 2 such that they intercept the Beam (E) of electromagnetic radiation on both sides of the Sample (SS).

It is noted that Reflectometer, Spectrophotometer Ellipsometer, Polarimeter, Mueller Matrix Measuring System and the like systems can be generically termed "material system investigating systems".

It is also noted that it is within the scope of the invention to provide the angle-of-incidence changing system on only one side of a sample.

The terminology "focusing optics" is used in the Claims to indicate that any optics, lens or mirror, can be applied to focus and/or re-collimate an electromagnetic beam.

Figure 18A:
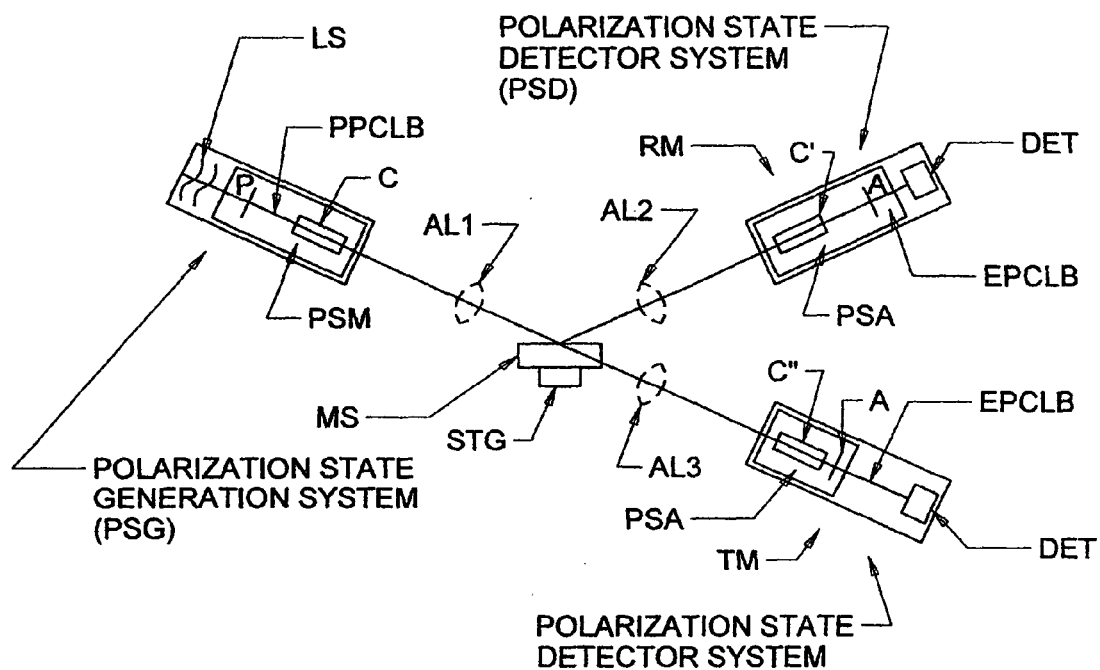
FIG. 18a shows a diagram of an ellipsometer system with both reflection and transmission detectors.

For general insight FIG. 18a shows a diagram of an ellipsometer/polarimeter system for use in both reflection (RF) and transmission (TM) modes. A source of monochromatic or polychromatic electromagnetic radiation (LS) is shown to, via polarization state modifier (PSM), which is demonstrated as being comprised of a Polarizer (P) and optionally a Compensator (C), provide a polarized beam of electromagnetic radiation (PPCLB) which is directed to interact with a material system (MS) which is placed on a stage (STG). (Note that conventional terminology identifies a Polarization State Generation System (PSG) as a combination of said source of monochromatic or polychromatic electromagnetic radiation (LS) and a Polarization State Modifier (PSM), which Polarization State Modifier (PSM) is demonstrated as being comprised of a Polarizer (P) and optionally a Compensator (C)). After interaction with the material system (MS), propagated electromagnetic beam (PPCLB) emerges as (EPCLB), after passing through a polarization state analyzer (PSA) and enters a detector system (DET). (Note that conventional terminology provides that for each of the Reflection (RM) and Transmission (TM) Modes, a Polarization State Analyzer (PSA) is demonstrated as being comprised of an Analyzer (A) and optionally a Compensator (C') or (C'') respectively, and that when said Polarization State Analyzer (PSA) is combined with a Detector System (DET), there is formed a Reflection or Transmission Mode Polarization State Detector System (PSD), respectively). It is also to be understood that if the Polarization State Modifier (PSM), and Polarization State Analyzer (PSA) are not present, then FIG. 18a demonstrates a Spectrophotometer system comprised of (LS), (STG/(MS) and (DET). It is to be understood that the angle of incidence of the electromagnetic beam (PPCLB) is often oriented closer to normal to the material sample (MS) upper surface, when the system is operated as a Spectrophotometer. With regard to the present invention, it is to be appreciated that the Detector System(s) (DET) indicated can be multiple detector systems mounted on a positionable means (eg. a movable arm), thereby allowing easy alternate positioning of the Detector Systems in at least two locations. Note that such a rotation would be in a vertically oriented plane, but that this is only demonstrative and in any embodiment of the present invention multiple detector system, motion in any plane is within the scope of the Claims. In addition, it is noted that variously shaped apertures and/or focusing lenses (AL1) (AL2) (AL3), preferably achromatic, can be, but are not necessarily present before and/or after a sample as can functional equivalents to the polarizer/compensator/analyzer combinations.

Figure 18B:
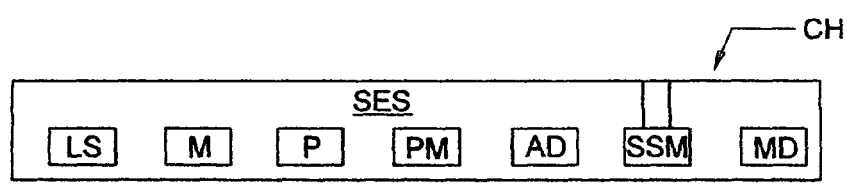
FIG. 18b shows a chamber (CH) which contains an essentially enclosed space (SES), with functional blocks corresponding to J.A. Woollam Co. VUV-VASE components therewithin.

There is shown in FIG. 18b a chamber (CH) which contains a substantially enclosed space (SES). Within said substantially enclosed space (SES) are shown functional blocks corresponding to Vacuum-Ultra-Violet Variable Angle Spectroscopic Ellipsometer (VUV-VASE) components. In particular, in said substantially enclosed space (SES) there is sequentially shown a source of polychromatic electromagnetic radiation (LS), a Monochromator (M), a polarization state setting means for setting a polarization state in at least a selected small range of wavelengths in a beam including ultraviolet wavelength range electromagnetic radiation (P); a means which enables sequentially modifying a polarization state set by said polarization state setting means, through a plurality of polarization states (PM); an alignment detector means (AD) which can comprise a plurality of detector elements surrounding a substantially centrally located hole through which a beam of electromagnetic radiation can pass, an indication of a subspace sequestering means (SSM) comprising means for placing and maintaining a sample in a desired position and orientation in a subspace sequestering means; and a multiple detector system (MD).

It should be appreciated that while the Monochromator (M) is shown in a specific position in FIG. 18b, but except for the source of electromagnetic radiation which must, of course be prior to the sample, can be moved to other locations in the system and be functional. Further, where Infrared wavelengths are desired, the source of polychromatic electromagnetic radiation (LS) and the Monochromator system can be replaced by an Infrared Fourier Transform (IR-FTIR) source system. And in addition, where a spectroscopic range of wavelengths of electromagnetic radiation are simultaneously utilized the monochromater can be deleted from FIG. 18b.

Figure 18C:
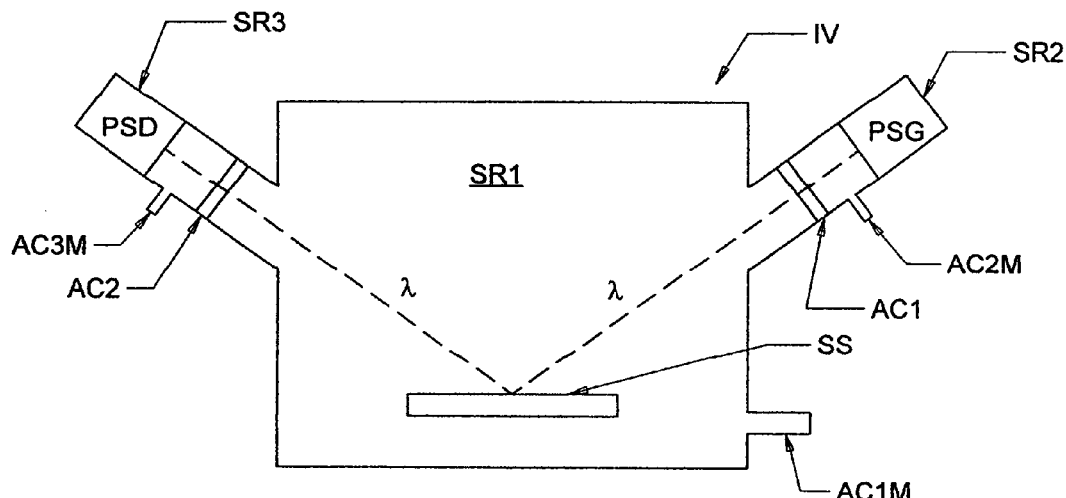
FIG. 18c demonstrates that an environmental control chamber can comprises multiple regions in which can be separately, or commonly sequestered Polarization State Generation System (PSG), Sample (SS) and Polarization State Generation Detector (PSD).

FIG. 18c demonstrates that an environmental control chamber can comprise multiple regions which can be separately sequestered. Shown are separate regions in which are present a Sample (SS), a Polarization State Generator (PSG) and a Polarization State Detector (PSD). Note that Ambient Control Means (AC1M), (AC2M) and (AC3M) are associated with said sequestered regions ((SR1), (SR2) and (SR3) respectively and allow entry of purging gas or evacuation of their associated sequestered region. Sequestering Means (AC1) and (AC2), (eg. windows), separate the Sequestered Regions (SR2) from (SR1) and (SR1) from (SR3) respectively. The environment in each sequestered region can then be separately controlled.

Figure 18D:
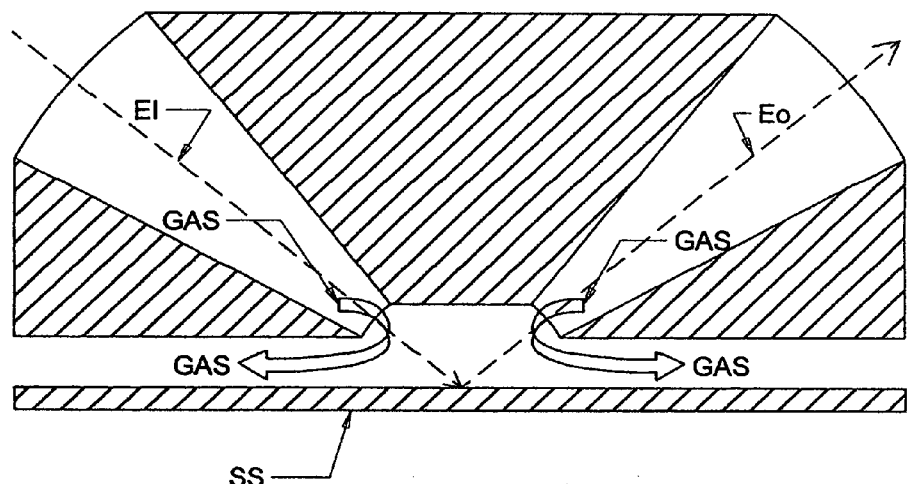
FIG. 18d demonstrates a system for flowing gas in the vicinity of a surface of a sample as described in U.S. Pat. No. 6,813,026 to McAninch.

FIG. 18d demonstrates a system for flowing gas in the vicinity of a surface of a sample as described in U.S. Pat. No. 6,813,026 to McAninch. Note that it is indicated as being entered through the "tubes" that allow electromagnetic radiation to enter and exit.

Figure 19:
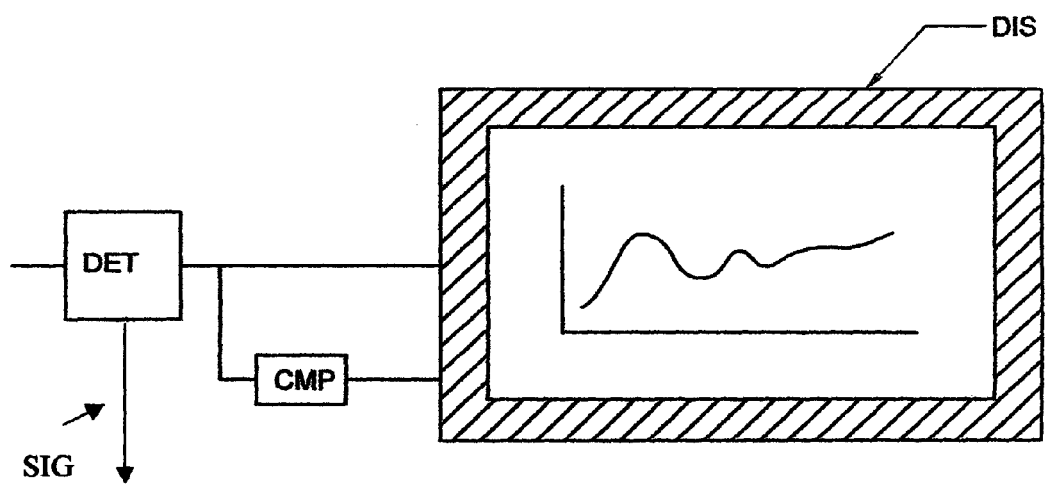
FIG. 19 is included to demonstrate that at least some data provided by the data detector (DET) and/or analyzed variations thereof can be displayed on a Display Means (DIS) or by other display means and/or at least some of the data obtained from said detector can be stored in machine readable media and/or cause at least some obtained data to be represented by a signal which is applied to provide a concrete and tangible result.

Finally, FIG. 19 demonstrates that data provided by the Data Detector (DET) and/or the results of analysis thereof by such as a Computer (CMP), can be displayed on a Display Means (DIS), or otherwise during practice of the methodology of the present invention. In general, FIG. 19 is included to indicate that at least some of the data from said detector and/or an analyzed version thereof can be stored in machine readable media and/or displayed electronically or by non-electronic means, and/or can be caused to be represented by a signal which is applied to provide a concrete and tangible result, such as control of a fabrication process.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for positioning a source of a beam of electromagnetic radiation and a detector thereof in relation to a sample to be investigated comprising:
    a source and detector of electromagnetic radiation and a sample;
said system further comprising means for effecting relative translational motion between said source and detector of electromagnetic radiation and said sample in three orthogonally related dimensions with respect to a surface of said sample, which can be oriented in any plane in laboratory coordinates;
said system further comprising means for effecting rotational motion of said source and detector of electromagnetic radiation about at least one axis;
said system further comprising at least one electromagnetic beam intercepting angle-of-incidence changing system comprising elements which are easily functionally entered into the locus of the electromagnetic beam on both sides of said sample system, which at least one electromagnetic beam intercepting angle-of-incidence changing system serves to direct said electromagnetic beam onto substantially the same spot on the sample system as is the case where the said at least one electromagnetic beam intercepting angle-of-incidence changing system is not functionally present, but at an angle-of-incidence which is different than that when said at least one electromagnetic beam intercepting angle-of-incidence changing system is not functionally present, said at least one electromagnetic beam intercepting angle-of-incidence changing system not effecting, or requiring change of, the locus of the electromagnetic beams outside said at least one electromagnetic beam intercepting angle-of-incidence changing system, on either side of said means for supporting a sample system, hence does not require said material system investigating system to comprise multiple sources and detectors or the change of position of at least one selection from the group consisting of:
    said source of electromagnetic radiation; and
    said detector thereof;
to effect change said angle-of-incidence.

2. A system as in claim 1 wherein said means for effecting rotational motion of said source and detector of electromagnetic radiation about at least one axis, comprises means for causing rotation about at least two orthogonally oriented axes.

3. A system as in claim 1 wherein said source and detector of electromagnetic radiation are mounted in fixed relationship to one another.

4. A system as in claim 1 wherein said source and detector of electromagnetic radiation comprises a polarization state generator and a polarization state detector mounted in fixed relationship to one another.

5. A system as in claim 1 which is characterized as being a selection from the group consisting of:
    reflectometer;
    rotating analyzer ellipsometer;
    rotating polarizer ellipsometer;
    rotating compensator ellipsometer;
    modulation element ellipsometer;
    Mueller Matrix measuring system.

6. A system as in claim 5, in which the selection from the group consisting of:
    reflectometer;
    rotating analyzer ellipsometer;
    rotating polarizer ellipsometer;
    rotating compensator ellipsometer;
    modulation element ellipsometer;
    Mueller Matrix measuring system;
is spectroscopic in that it operates at a multiplicity of wavelengths.

7. A system as in claim 1, which further comprises attached cable means for at least one selection from the group consisting of:
    providing electrical power; and
    transmitting data from said data detector means.

8. A system as in claim 1, which further comprises an on-board battery source of electric power.

9. A system as in claim 1, which further comprises an on-board wireless transmitter for transmitting data from said data detector means.

10. A system as in claim 1, in which said system is a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one Pseudo-Achromatic compensator(s) positioned at a location selected from the group consisting of:
    before said stage for supporting a material system;
    after said stage for supporting a material system; and
    both before and after said stage for supporting a material system.

11. A system as in claim 1, in which said said selected system further comprises means for flowing purging gas onto said sample at a location thereon at which at least one selection from the group consisting of electromagnetic radiation of:
    UV and;
    IR wavelengths;
is caused to impinge.

12. A system as in claim 1, in which said at least one electromagnetic beam intercepting angle-of-incidence changing system comprises, on each side of said means for supporting a sample system, at least one selection from the groups consisting of:
    multiple angle prism(s); and
    a system of mirrors;
said at least one electromagnetic beam intercepting angle-of-incidence changing system being slidably mounted to a guide element such that the functional presence thereof in the pathway of the locus of the electromagnetic beams on both sides of said means for supporting a sample system is effected by physical sliding motion of said at least one electromagnetic beam intercepting angle-of-incidence changing system along said guide element.

13. A system as in claim 1, in which said at least one electromagnetic beam intercepting angle-of-incidence changing system comprises a first multiangle prism on the incident side of said means for supporting a sample system and a second multiangle prism thereafter, said first and second multiangle prisms each having a first and a second side, each said multiangle prism presenting with first and second inner surfaces associated with said first and second sides, respectively, the first and second side of each multiangle prism having means for changing the properties of inner surface thereof from essentially transmissive to essentially reflective, each said multiangle prism being oriented such that an electromagnetic beam entering thereinto encounters the first or second inner surface thereof and either passes therethrough and progresses on to contact a sample system placed on said means for supporting a sample system, or reflects from said first or second inner surface thereof and then from said second or first inner surface thereof, respectively, and then progresses on to contact a sample system placed on said means for supporting a sample system.

14. A system as in claim 13, which further comprises at least one shutter door which can be opened to let the electromagnetic beam pass, or closed to block its passage, said at least one shutter door being positioned in the electromagnetic beam locus selected from the group consisting of:
    defined by passage through said first or second side of said first multiangle prism; and
    defined by reflection from said first or second side of said first multiangle prism;
said at least one shutter door being positioned between at least one selection from the group consisting of:
    said first multiangle prism and the means for supporting a sample system; and
    said means for supporting a sample system and said second multiangle prism.

15. A system as in claim 1, in which said at least one electromagnetic beam intercepting angle-of-incidence changing system comprises, on first and second sides of said means for supporting a sample system, first and second beam splitters, respectively, which first and second beam splitters each pass approximately half, and reflect approximately half of a beam of electromagnetic radiation caused to be incident thereupon at an oblique angle to a surface thereof; said at least one electromagnetic beam intercepting angle-of-incidence changing system further comprising a first reflective means positioned to intercept the approximately half of the electromagnetic beam which reflects from said first beam splitter on the incident side of said means for supporting a sample system and direct it toward said means for supporting a sample system; and also further comprising a second reflective means positioned after said means for supporting a sample system to intercept an electromagnetic beam which reflects from a sample system placed on said means for supporting a sample system and direct it toward the second beam splitter;
    said material system investigating system further comprising at least one shutter door which can be opened to let the electromagnetic beam pass, or closed to block its passage, said at least one shutter door being positioned in the pathway of the electromagnetic beam between which progresses along a locus selected from the group consisting of:
        defined by passage through said first beam splitter; and
        defined by reflection from said first beam splitter;
    on either side of said means for supporting a sample system.

16. A system as in claim 1, which includes at least two multiple angle prisms, one being present on one side of said sample system, and the other thereof being present on the other side of said sample system.

17. A system as in claim 1, which includes focusing optic positioned to focus a beam of electromagnetic radiation onto a sample system.

18. A system as in claim 1, which includes means for adjusting the orientation of at least one electromagnetic beam intercepting angle-of-incidence changing system, optionally in simultaneous combination which includes focusing optics positioned to focus a beam of electromagnetic radiation onto a sample system and recollimate the beam of electromagnetic radiation which reflects from said sample system.

19. A system as in claim 1, in which the at least one electromagnetic beam intercepting angle-of-incidence changing system comprises, on at least one side selected from the group consisting of:
    said first and;
    said second;
sides of said means for supporting a sample system, at least one system of mirrors, said at least one system of mirrors being comprised of:
a means for changing the propagation direction of an initial beam of electromagnetic radiation without significantly changing the phase angle between orthogonal components thereof, said means comprising two pairs of reflecting mirrors oriented so that said initial beam of electromagnetic radiation reflects from a first reflecting means in the first pair of reflecting means to a second reflecting means in said first pair of reflecting means, in a first plane; and such that the beam of electromagnetic radiation which reflects from the second reflecting means in said first pair of reflecting means reflects from the first reflecting means in said second pair of reflecting means to said second reflecting means in said second pair of reflecting means, in a second plane which is essentially orthogonal to said first plane; such that the direction of propagation of the beam of electromagnetic radiation reflected from the second reflecting means in said second pair of reflecting means is different from the propagation direction of the initial beam of electromagnetic radiation; the basis of operation being that changes entered between the orthogonal components by the first pair of reflective means is canceled by that entered by the second pair of reflective means.

20. A system as in claim 1 in which the means for setting the angle of incidence of a beam of electromagnetic radiation comprises, as viewed in elevation, first and second arms pivotally interconnected to one another at an upper aspect thereof by a first pivot means, said first and second arms projecting downward and to the left and right of said first pivot means; distal ends of said first and second arms being pivotally affixed to third and forth arms, said third and forth arms being pivotally interconnected to one another by a second pivot means at a lower aspect thereof, said third and forth arms being projected upward and to the left and right of said second pivot means at said lower aspect thereof; there being at least two substantially downward projecting arms pivotally afixed to each of said third and forth arms, distal ends of which are pivotally affixed to fifth and sixth arms which are not interconnected to one another, but project upward to the left and right, respectively;

there being affixed to one of said fifth and sixth arms a source of a beam of electromagnetic radiation, and to the other of said sixth and fifth arms a detector of said beam of electromagnetic radiation;

there further being a sample located such that a beam of electromagnetic radiation produced by said source of a beam of electromagnetic radiation reflects from an upper surface of said sample and enters said detector of said beam of electromagnetic radiation;

such that in use when the first pivot means at which said first and second arms are interconnected is caused to be vertically raised or lowered, the angle of incidence at which the beam of electric radiation approaches said sample surface is changed, but the location at which it interacts with said sample surface remains substantially unchanged.

21. A system as in claim 1 in which the electromagnetic beam intercepting angle-of-incidence changing system comprises elements which are easily functionally entered into the locus of the electromagnetic beam on one side of said sample system, which one electromagnetic beam intercepting angle-of-incidence changing system serves to direct said electromagnetic beam to, or receive said electromagnetic beam from substantially the same spot on the sample system as is the case where the said one electromagnetic beam intercepting angle-of-incidence changing system is not functionally present.

22. A system as in claim 1 which further comprises interface means that provides actual or substantial slidable contact with said sample or a separate stage for supporting said sample, such that a mini-chamber is formed thereby;

said system further comprising means for introducing gas into said mini-chamber;

such that in use said mini-chamber is caused to access, contain or make actual or substantial slidable contact with a portion of said sample or a support therefore.

23. A system for application in investigating a sample system with electromagnetic radiation, sequentially comprising:

a. a source of a beam electromagnetic radiation;
    b. a polarizer element;
    c. optionally a compensator element;
    d. additional element(s);
    e. a sample system;
    f. additional element(s);
    g. optionally a compensator element;
    h. an Analyzer element; and
    i. a Detector System;

wherein said additional component(s) in d. and f. each comprise at least one electromagnetic beam intercepting angle-of-incidence changing system element which can be easily entered into the locus of the electromagnetic beam on both sides of said sample system, which at least one electromagnetic beam intercepting angle-of-incidence changing system elements serves to direct said electromagnetic beam onto substantially the same spot on the sample system as is the case where the said at least one electromagnetic beam intercepting angle-of-incidence changing system elements are not present, but at an angle-of-incidence which is different than that when said at least one electromagnetic beam intercepting angle-of-incidence changing system is not present, said at least one electromagnetic beam intercepting angle-of-incidence changing system elements not effecting, or requiring change of, the locus of the electromagnetic beams outside said at least one electromagnetic beam intercepting angle-of-incidence changing system elements, on either side thereof, hence does not require multiple sources and detectors or change of position of at least one selection from the group consisting of:

said source of electromagnetic radiation; and
    said detector thereof;

to effect change said angle-of-incidence;

said material system investigating system being functionally mounted to a two dimension location means for positioning said selected system at points in an two dimensional plane which is, in use, oriented substantially parallel to but offset from, the plane of a surface of said sample system;

such that in use said selected system is located near the surface of said sample and a beam of electromagnetic radiation provided by said source means is caused to interact therewith and enter said data detector means;

said selected system further comprising means for adjusting the location thereof at desired third dimension offset locations with respect to points in said plane of the surface of said sample;

said selected system further comprising means for controlling the location of the source means and data detector means in said two dimension plane; and said system further comprising at least one selection from the group consisting of:

means for effecting rotational motion of said source and detector of electromagnetic radiation about at least one axis; and means for providing introducing gas near said sample.

24. A system as in claim 23, in which each electromagnetic beam intercepting angle-of-incidence changing system is a selection from the group consisting of:

multiangle prisms; and
    a plurality of mirrors.

25. A system for positioning a source of a beam of electromagnetic radiation and a detector thereof in relation to a sample to be investigated comprising:

a source and detector of electromagnetic radiation and a sample;

said system further comprising means for effecting relative translational motion between said source and detector of electromagnetic radiation and said sample in three orthogonally related dimensions with respect to a planar or non-planar surface of said sample, which can be in any orientation in laboratory coordinates;

said system further comprising at least one electromagnetic beam intercepting angle-of-incidence changing system comprising elements which are easily functionally entered into the locus of the electromagnetic beam on both sides of said sample system, which at least one electromagnetic beam intercepting angle-of-incidence changing system serves to direct said electromagnetic beam onto substantially the same spot on the sample system as is the case where the said at least one electromagnetic beam intercepting angle-of-incidence changing system is not functionally present, but at an angle-of-incidence which is different than that when said at least one electromagnetic beam intercepting angle-of-incidence changing system is not functionally present, said at least one electromagnetic beam intercepting angle-of-incidence changing system not effecting, or requiring change of, the locus of the electromagnetic beams outside said at least one electromagnetic beam intercepting angle-of-incidence changing system, on either side of said means for supporting a sample system, hence does not require said material system investigating system to comprise multiple sources and detectors or the change of position of at least one selection from the group consisting of:

said source of electromagnetic radiation; and
said detector thereof;

to effect change said angle-of-incidence.

26. A system as in claim 25 which further comprises means for effecting rotational motion of said source and detector of electromagnetic radiation about at least one axis.

27. A system for positioning a source of a beam of electromagnetic radiation and a detector thereof in relation to a sample to be investigated comprising:

a source and detector of electromagnetic radiation and a sample;

said system further comprising means for effecting relative translational motion between said source and detector of electromagnetic radiation and said sample in three orthogonally related dimensions with respect to a planar or non-planar surface of said sample, which can be in any orientation in laboratory coordinates;

said system further comprising means for causing relative motion between said source and detector of electromagnetic radiation as a unit, and said sample;

said system further comprising interface means that provides means for introducing gas near said sample;

such that in use wavelengths which are absorbed by oxygen and/or water vapor can be applied;

said system further comprising at least one electromagnetic beam intercepting angle-of-incidence changing system comprising elements which are easily functionally entered into the locus of the electromagnetic beam on both sides of said sample system, which at least one electromagnetic beam intercepting angle-of-incidence changing system serves to direct said electromagnetic beam onto substantially the same spot on the sample system as is the case where the said at least one electromagnetic beam intercepting angle-of-incidence changing system is not functionally present, but at an angle-of-incidence which is different than that when said at least one electromagnetic beam intercepting angle-of-incidence changing system is not functionally present, said at least one electromagnetic beam intercepting angle-of-incidence changing system not effecting, or requiring change of, the locus of the electromagnetic beams outside said at least one electromagnetic beam intercepting angle-of-incidence changing system, on either side of said means for supporting a sample system, hence does not require said material system investigating system to comprise multiple sources and detectors or the change of position of at least one selection from the group consisting of:

said source of electromagnetic radiation; and
said detector thereof;

to effect change said angle-of-incidence.

28. A system as in claim 27 in which said interface means provides slidable contact or substantial slidable contact between said source and detector and said sample and/or a stage upon which it is supported, such that a mini-chamber which accesses said sample is formed thereby.

29. A system as in claim 27 which further comprises means for effecting rotational motion of said source and detector of electromagnetic radiation about at least one axis.

30. A system for positioning a source of a beam of electromagnetic radiation and a detector thereof in relation to a sample to be investigated comprising:

a source and detector of electromagnetic radiation; and
a sample;

said system further comprising means for effecting translational motion of said source and detector of electromagnetic radiation with respect to a surface of said sample, along a translational axis;

said source and detector of electromagnetic radiation being sequentially aligned along said translational axis; and said system further comprising means for effecting rotational motion of said source and detector of electromagnetic radiation about said translational axis.

31. A system as in claim 30 which further comprises a hollow pipe and in which the means for effecting translational motion of said source and detector of electromagnetic radiation is applied to extend said source and detector into the hollow area inside thereof, and said means for effecting rotational motion of said source and detector of electromagnetic radiation about said translational axis can be applied to allow monitoring any surface position inside said pipe through an arc of up to a full 360 degree rotation.

32. A system as in claim 30 which further comprises a means for effecting translational motion of said source and detector of electromagnetic radiation, in a direction which is substantially perpendicular said translational axis.

* * * * *